United States Patent [19]
Nakamura

[11] Patent Number: 5,306,148
[45] Date of Patent: Apr. 26, 1994

[54] DENTAL POWER TOOL GUARD

[76] Inventor: Shoukou Nakamura, 61-2 Tsurukouji-machi,, Maebashi-shi, Gunma-ken, Japan

[21] Appl. No.: 970,359

[22] Filed: Nov. 2, 1992

[30] Foreign Application Priority Data

Nov. 6, 1991 [JP] Japan .................. 3-090721[U]
Jan. 16, 1992 [JP] Japan .................. 4-001136[U]

[51] Int. Cl.⁵ .................................................. A61C 1/16
[52] U.S. Cl. .......................................................... 433/116
[58] Field of Search .......................................... 433/116

[56] References Cited
U.S. PATENT DOCUMENTS

| | | | |
|---|---|---|---|
| 525,278 | 8/1894 | Peck | 433/116 |
| 1,004,118 | 9/1911 | Waters | 433/116 |
| 1,067,571 | 7/1913 | Abbott | 433/116 |
| 1,101,947 | 6/1914 | Morgan | 433/116 X |
| 2,307,677 | 1/1943 | Hawkinson | 433/116 |
| 2,671,269 | 3/1954 | Francis | 433/116 |
| 2,924,013 | 2/1960 | Wowra | 433/116 |
| 4,583,945 | 4/1986 | Labarde | 433/116 |

Primary Examiner—Gene Mancene
Assistant Examiner—Nicholas D. Lucchesi
Attorney, Agent, or Firm—Jordan and Hamburg

[57] ABSTRACT

A dental power tool is provided with a guard device incorporating a guard plate for keeping a possible obstacle, e.g. the tongue or a part of the inside wall of a lip, aside during the dental treatment.

2 Claims, 47 Drawing Sheets

DENTAL POWER TOOL GUARD

BACKGROUND OF THE INVENTION

The present invention relates to a dental power tool of e.g. air turbine operated or contra-angle type for cutting a decayed tooth.

For treatment on a decayed tooth, a combination is commonly utilized of a dental tool for cutting a decayed tooth, a vacuum nozzle for removing a pool of oral liquid produced during the treatment, and a mirror for keeping an obstacle, e.g. the tongue or a part of oral body, from disturbing the treatment.

More specifically, as shown in FIG. 54, the dental tool A and the mirror B are held by both the hands C, D of a dentist for treatment on a decayed tooth E while the vacuum nozzle F is gripped by the hand of a hygienist. This is a troublesome task and requires considerable cost. Also, appropriate cooperation between the dentist and the hygienist is essential for carrying out a dental treatment at efficiency.

However, the hygienists are substantially limited in number and not easily available because of today's labor shortage. For compensation, the dentist attempts to use the vacuum nozzle F for acting as the mirror B to keep the obstacles aside during cutting a decayed tooth or place it on the lip end of a patient. As a result, the pool of oral liquid will be removed unsuccessfully and/or the patient to be treated will feel unpleasant.

SUMMARY OF THE INVENTION

It is an object of the present invention, for eliminating the foregoing drawbacks, to provide an improved dental tool capable of cutting a decayed tooth efficiently without the help of a hygienist while giving no more discomfort to the patient.

The object and other objects and novel features of the present invention will be apparent from reading the following description in conjunction with the accompanying drawings.

It should be understood that the drawings are illustrative of the description and not limitative of the scope of the present invention.

DESCRIPTION OF THE PREFERRED EMBODIMENTS

Figure 1:
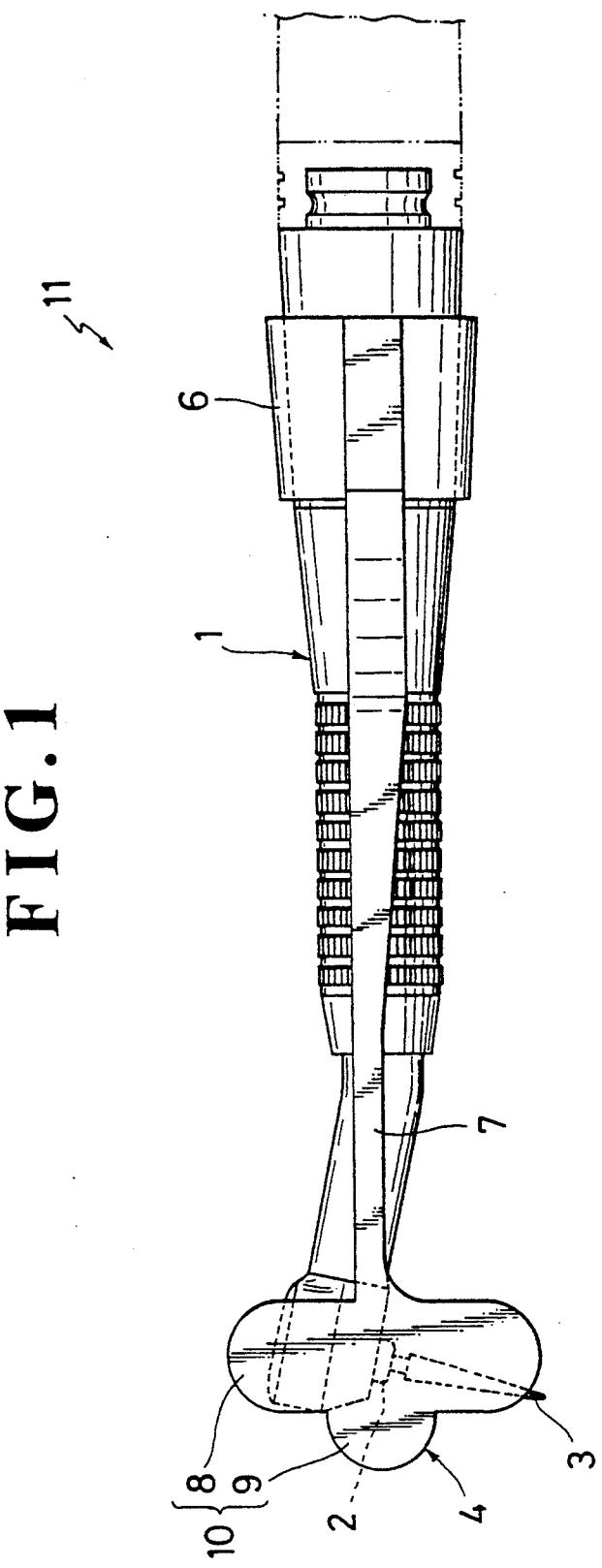
FIG. 1 is a side view showing a first embodiment of the present invention.
Figure 2:
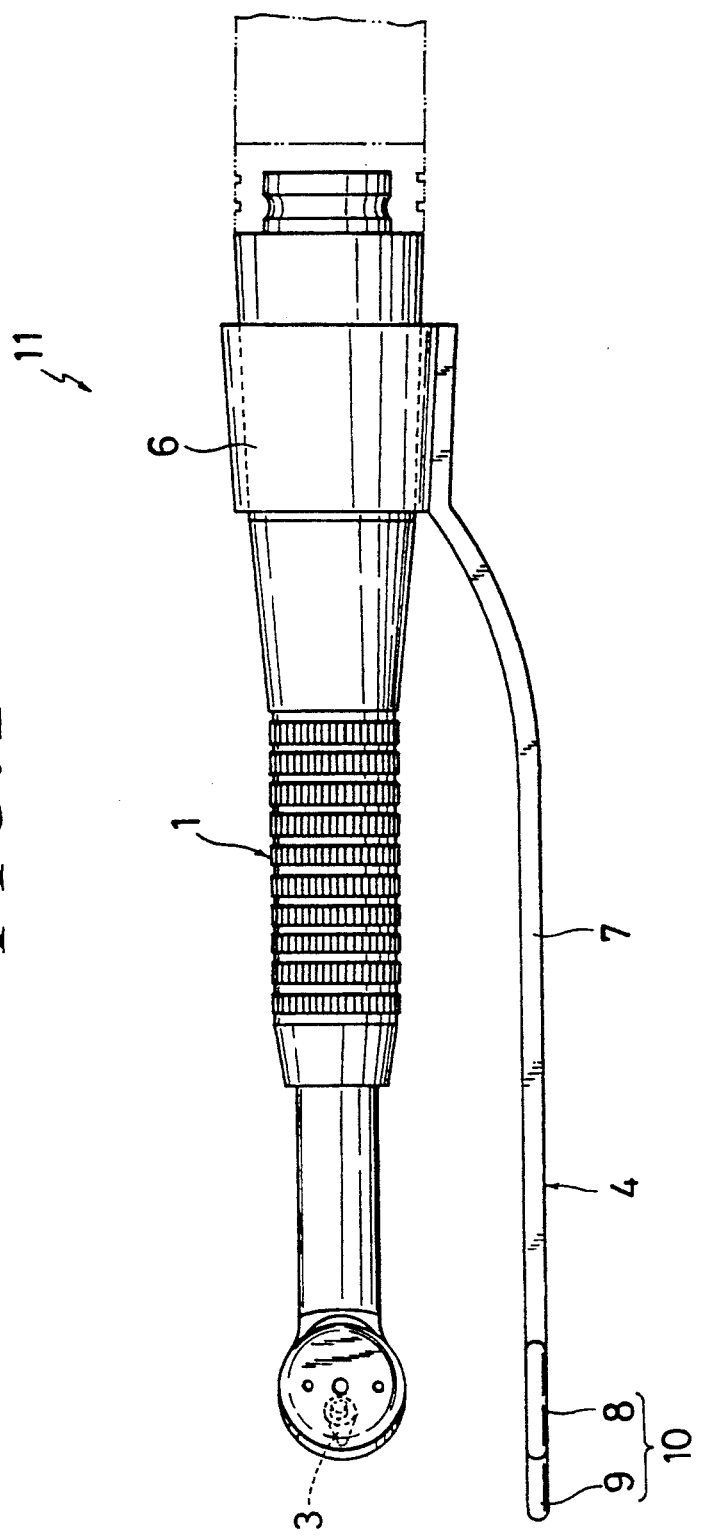
FIG. 2 is a plan view of the first embodiment of the present invention.
Figure 3:
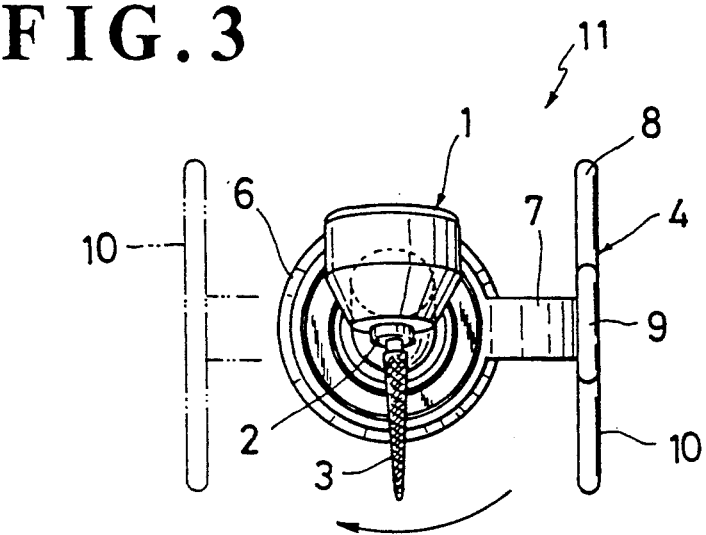
FIG. 3 is a front view of the first embodiment of the present invention.
Figure 4:
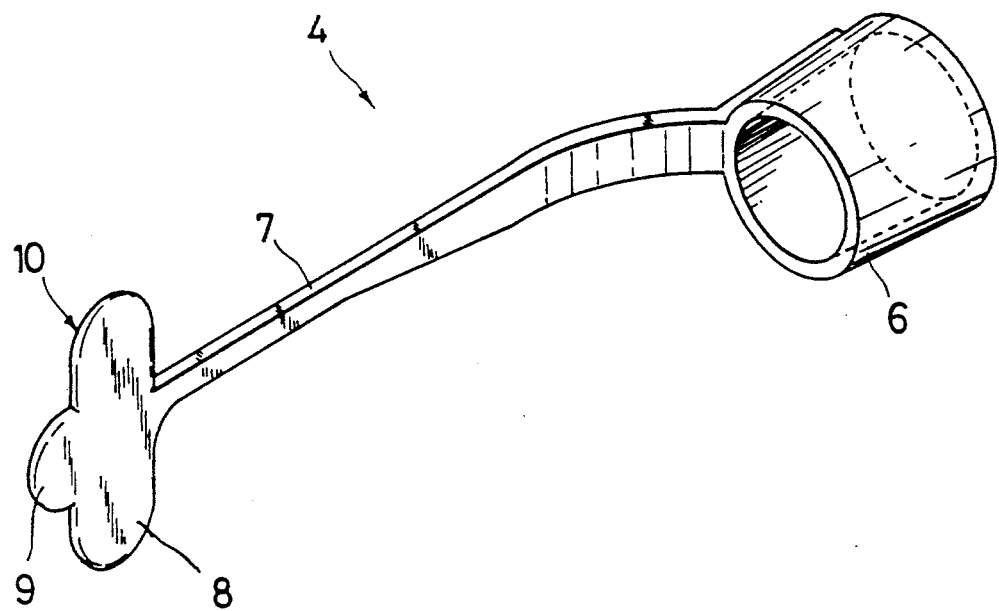
FIG. 4 is a perspective view of a guard device.

Preferred embodiments of the present invention will be described referring to the accompanying drawings.

According to a first embodiment of the present invention illustrated in FIGS. 1 to 10, there are provided a main body 1 of a dental power tool such as an air turbine hand-piece or motor-powered contra-angle rotary tool which provides at a front end a jet of water and can be held by hand, a high-speed rotary head 2 arranged at the front end of the dental tool body 1, and a cutting bit 3 detachably mounted to the high-speed rotary head 2.

There is also provided a guard device 4 which extends from the dental tool body 1 for keeping an obstacle, e.g. the tongue or inside wall of a lip, in the mouth away from the cutting bit 3 during the operation. The guard device 4 comprises a fitting ring 6 slidably fitted onto a tapered proximal portion of the dental tool body 1, an arm 7 fixedly mounted at rear end to the fitting ring 6 so as to extend towards the side of the cutting bit 3, and a guard plate 10 consisted of a vertical holding tab 8 mounted integrally to the front end of the arm 7 to extend upward and downward in half-round shape and a front holding tab 9 of half-round shape extending frontward from a central portion of the vertical holding tab 8.

Figure 5:
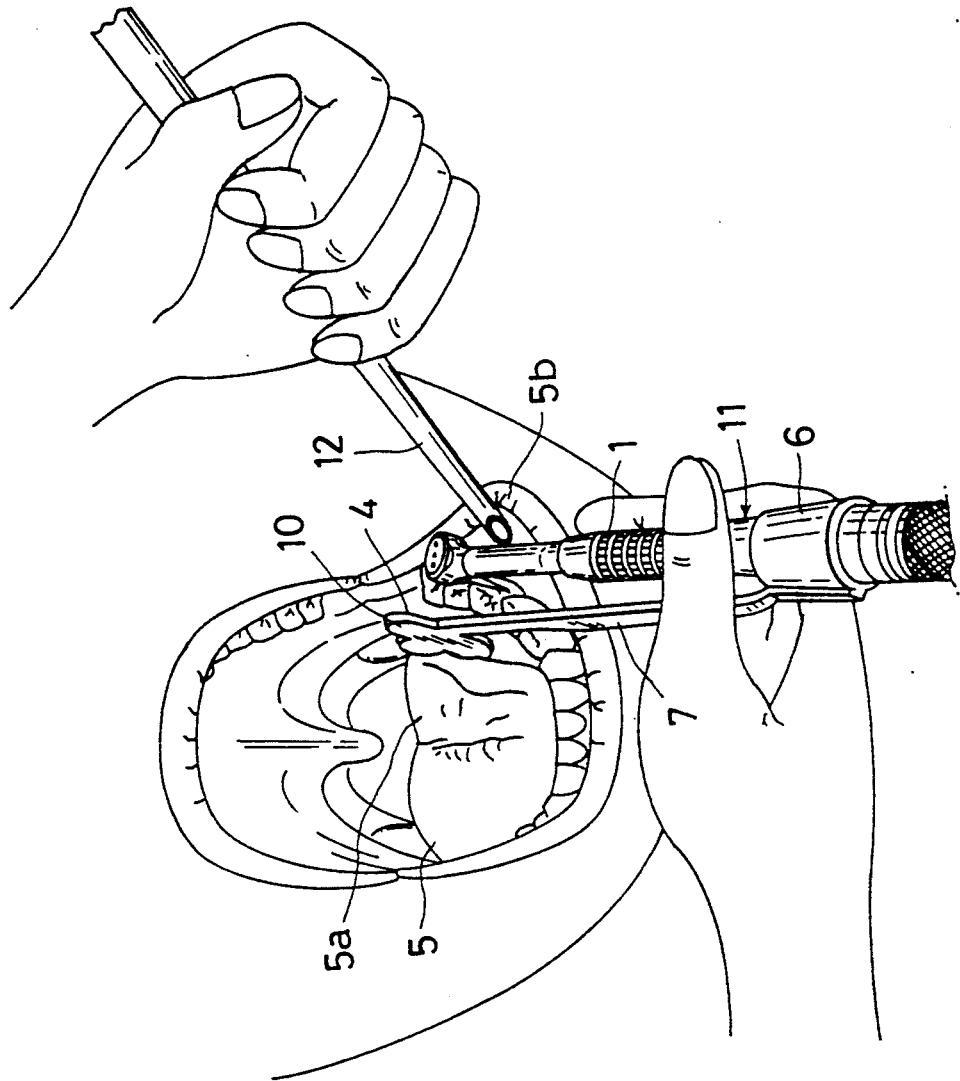
FIGS. 5 to 10 are explanatory views showing an application of the first embodiment of the present invention.

For dental treatment on a decayed tooth at the lower left as shown in FIG. 5, the foregoing assembly or dental tool 11 is operable with its guard plate 10 keeping the tongue 5a aside while a vacuum nozzle 12 is applied to the outside of the decayed tooth to be treated for keeping the inside wall 5b of a lower lip away and simultaneously, removing a pool of oral liquid.

Figure 6:
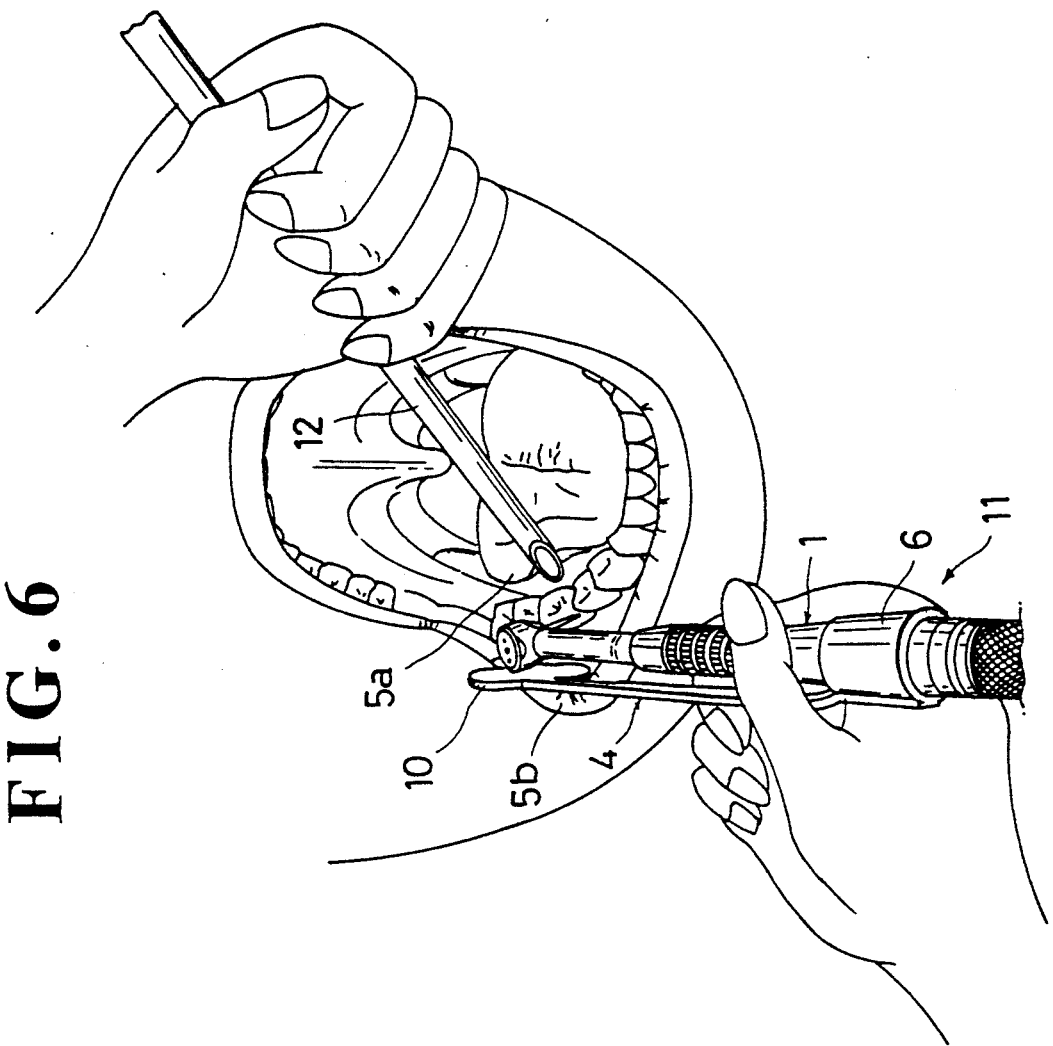

For dental treatment on a decayed tooth of at the lower right as shown in FIG. 6, the dental tool 11 is operable with its guard plate 10 keeping the lip inside wall 5b aside while the vacuum nozzle 12 presses against the tongue 5a and removes a pool of oral liquid.

Figure 7:
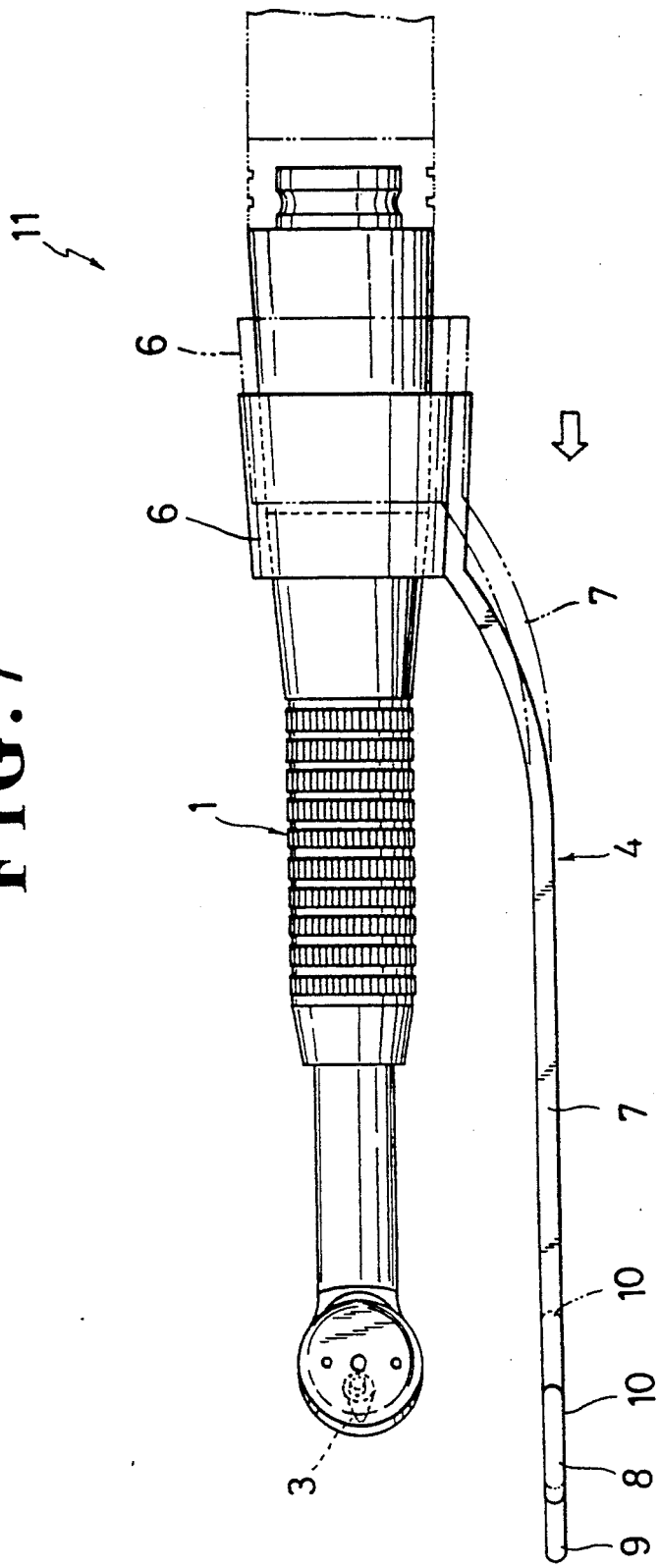
Figure 8:
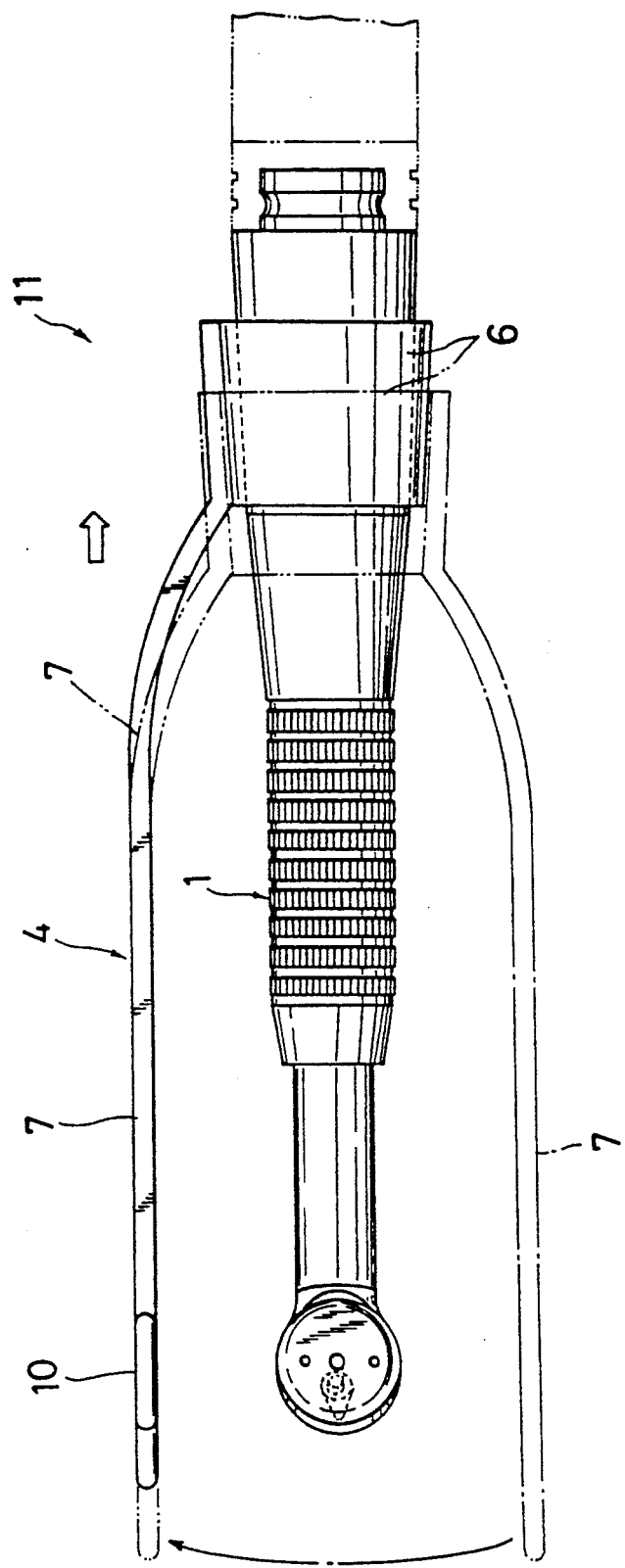

For the same purpose at the upper left of the dentition, the guard device 4 of the dental tool 11 is shifted by moving forward to disengage the fitting ring 6 from the dental tool body 1, turning the guard plate 10 through 180 degrees, and moving backward to fit the fitting ring 6 onto the dental tool body 1, as shown in FIGS. 7 and 8.

Figure 9:
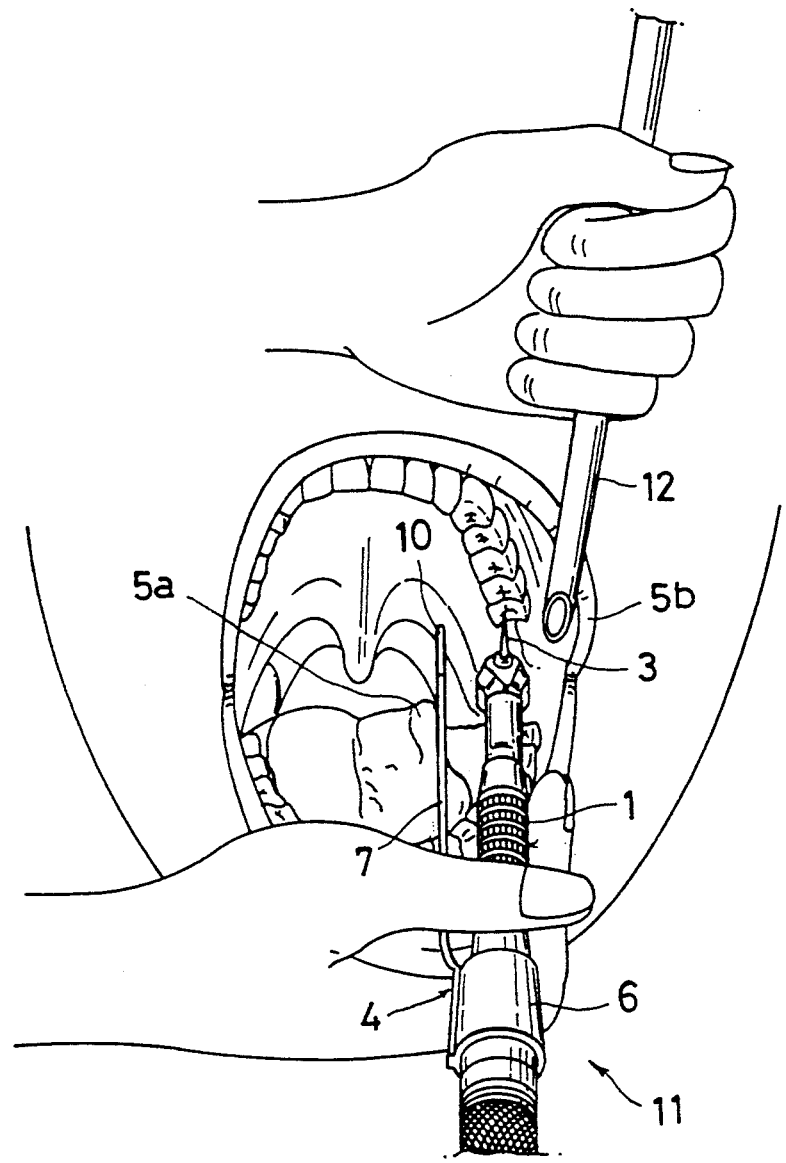
Figure 10:
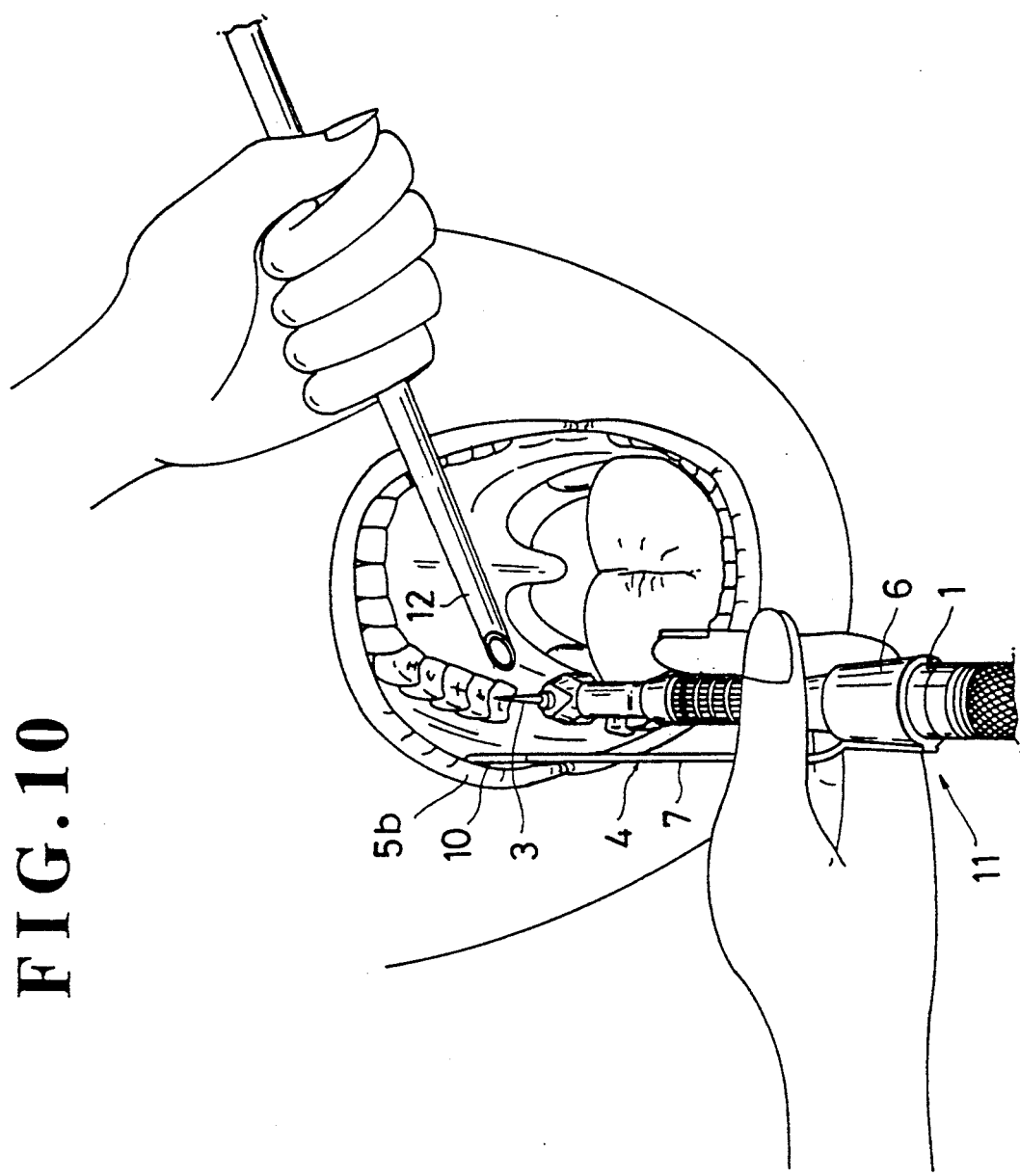
Figure 11:
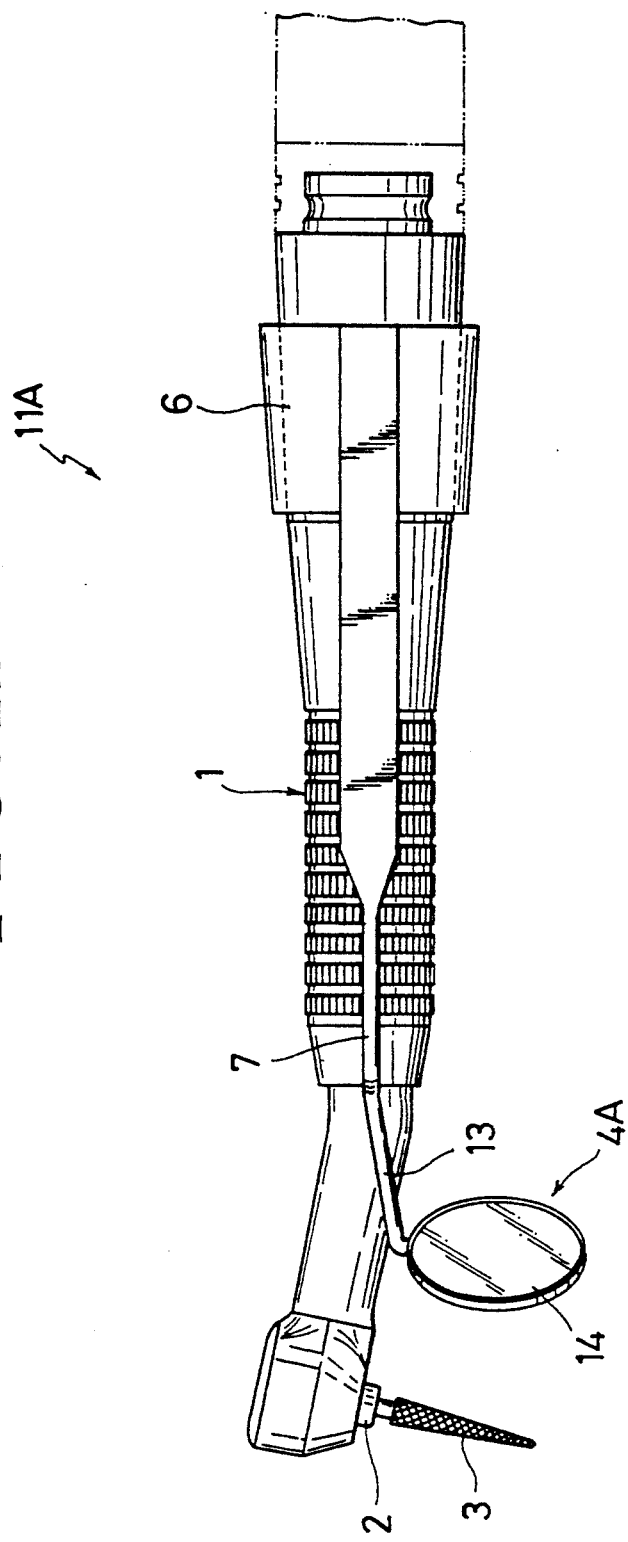
FIGS. 11 to 18 are explanatory views showing a second embodiment of the present invention.
Figure 12:
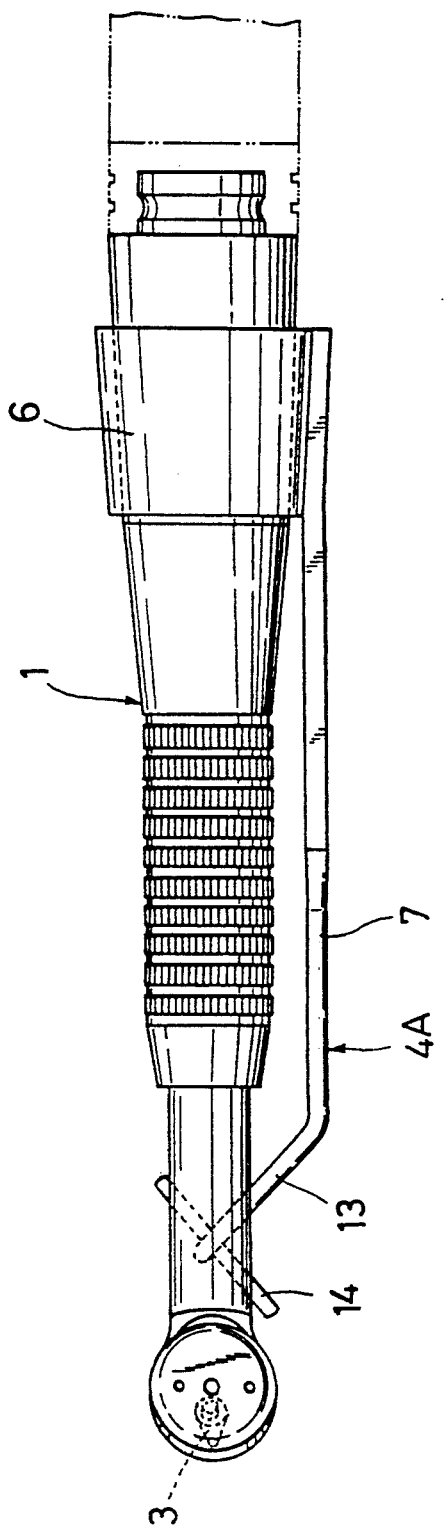
Figure 13:
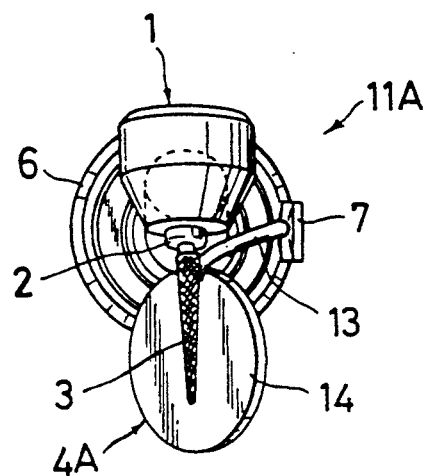
Figure 14:
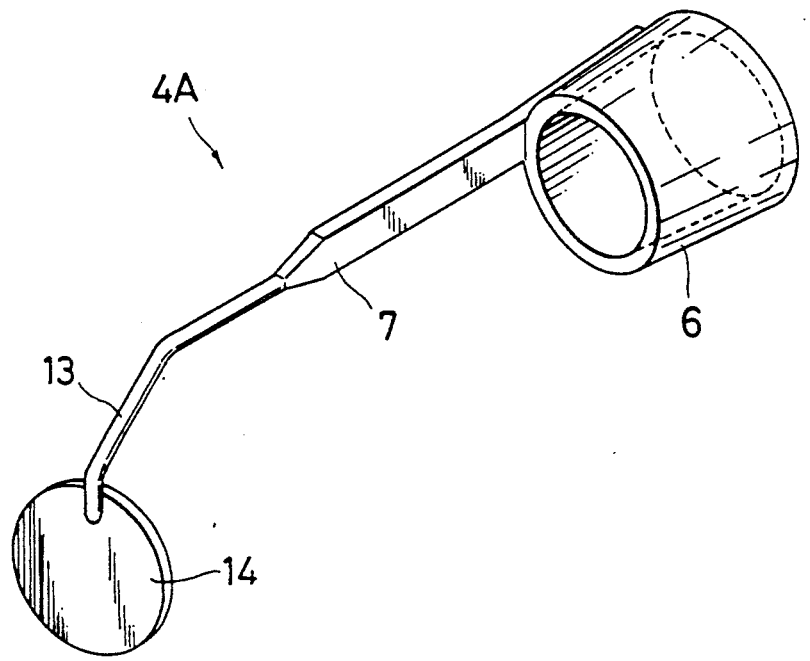

The treatment can then be carried out in an equal manner while the guard plate 10 keeps the tongue 5a aside and the vacuum nozzle 12 presses against the inside wall 5b of an upper lip, as shown in FIG. 9.

Similarly, the dental treatment at the upper right can be done while the guard plate 10 of the guard device 4 keeps the lip inside wall 5b and the vacuum nozzle 12 presses against the tongue 5a.

Other embodiments of the present invention will now be described referring to FIGS. 11 to 53. For ease of the description, like components as those in the first embodiment are denoted by like numerals and will not be explained further.

A second embodiment of the present invention shown in FIGS. 11 to 18 is differs from the first embodiment by the fact that the guard device 4 is replaced with a modified guard device 4A in which an arm 7 has a mirror 14 mounted by a bent portion 13 to the distal end thereof at an angle such that it is equally tilted when the arm 7 turns 180° and acts as the guard plate.

Figure 15:
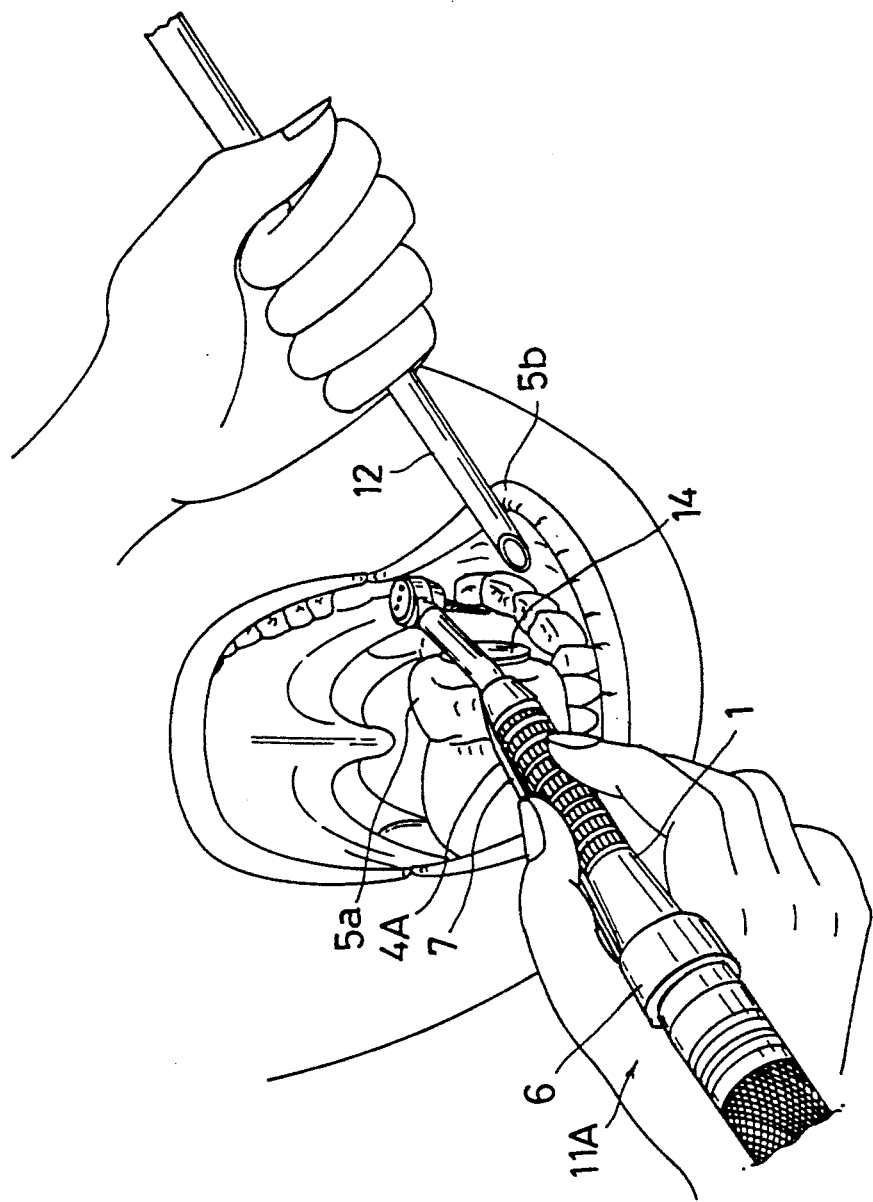
Figure 16:
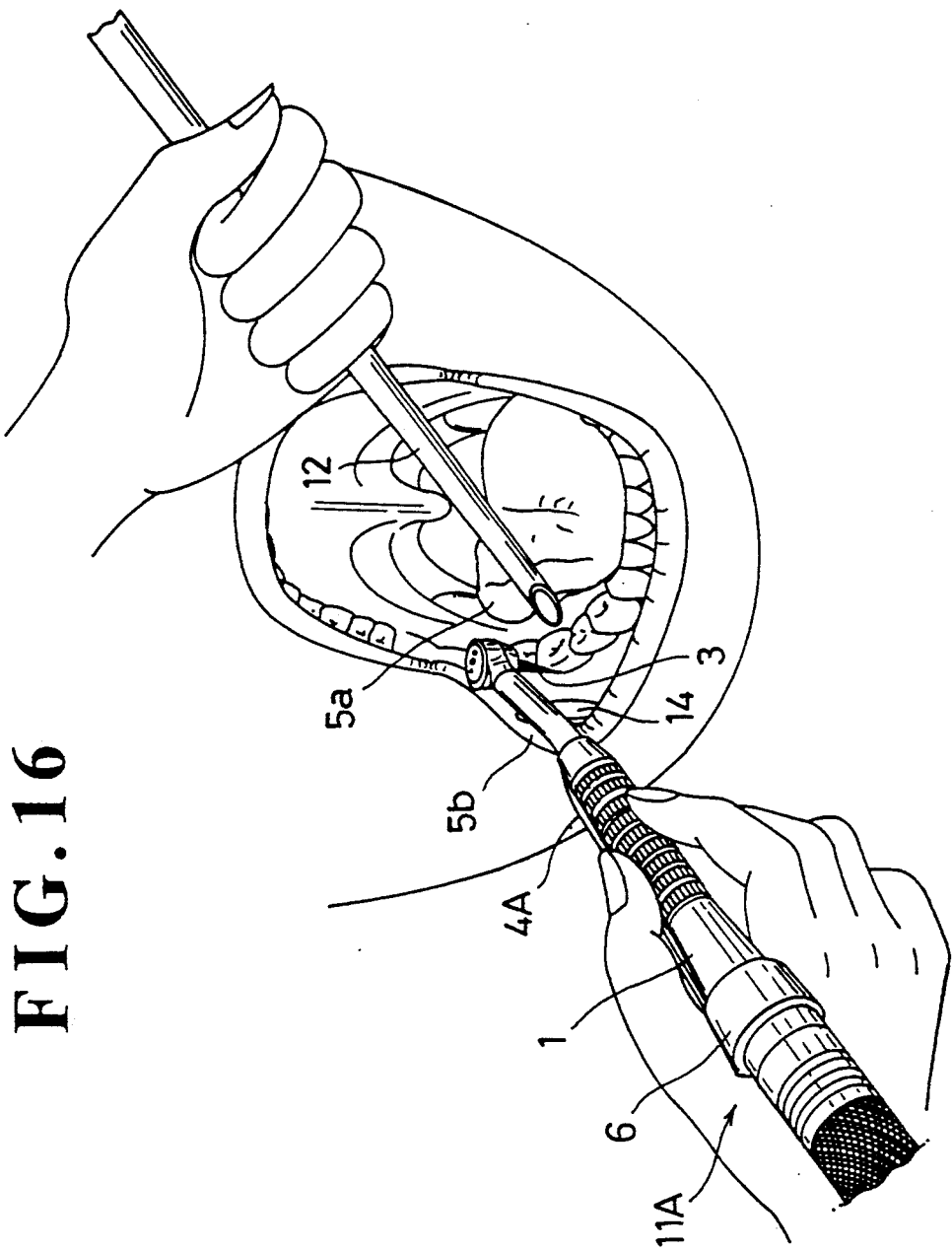
Figure 17:
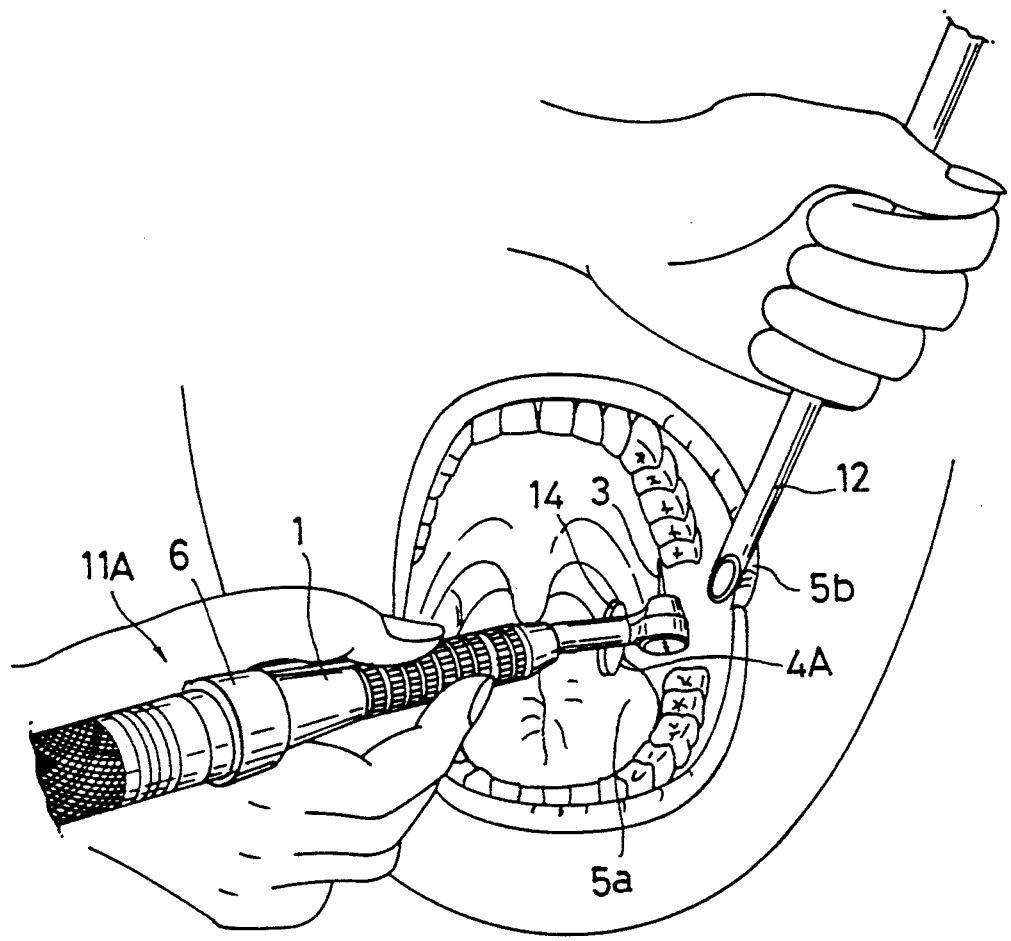
Figure 18:
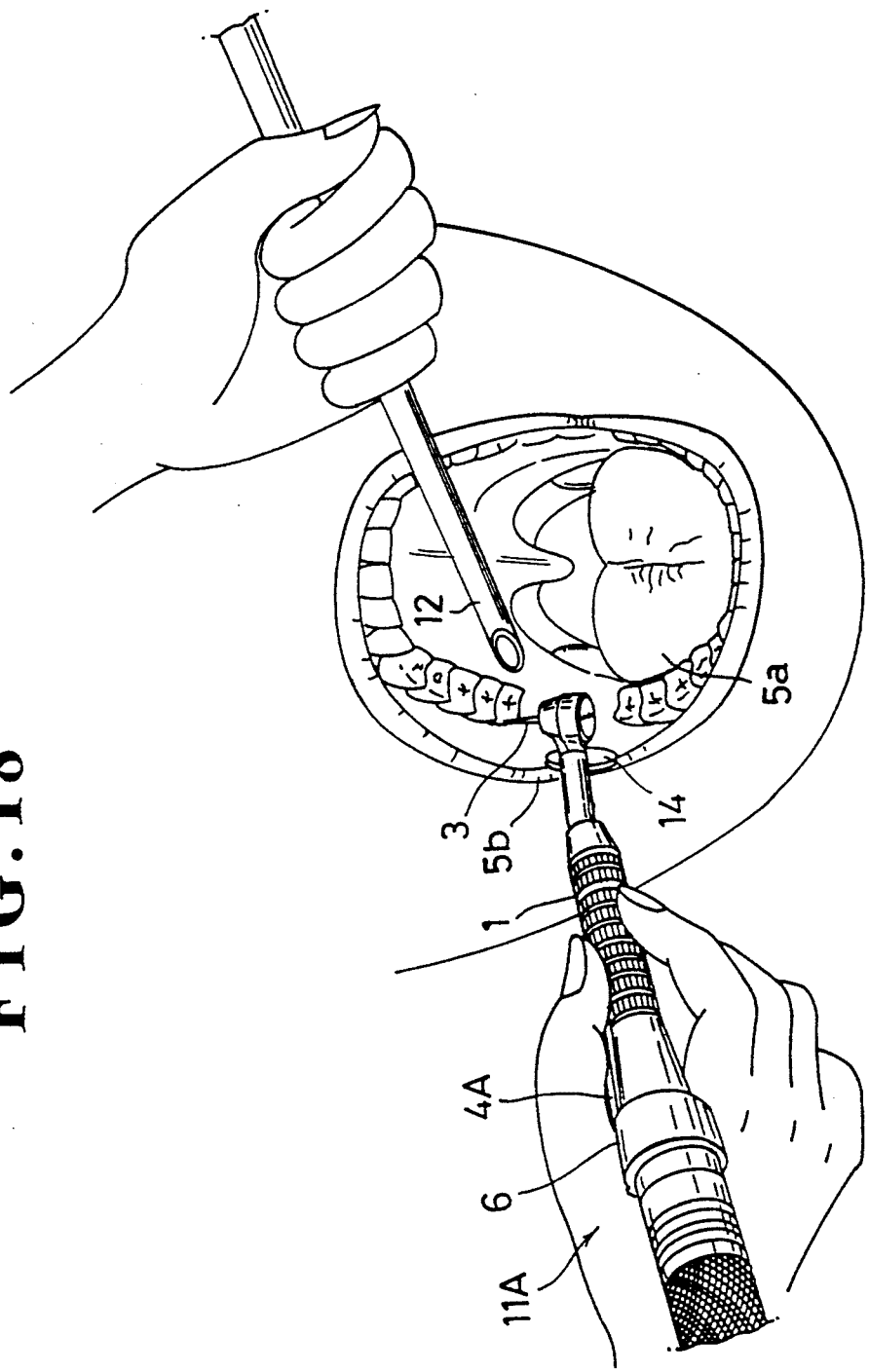

Accordingly, a dental tool 11A provided with the guard device 4A, like the dental tool 11 of the first embodiment, can successfully be used for treatment on a decayed tooth at the lower left, as shown in FIG. 15, at the lower right as shown in FIG. 16, at the upper left as shown in FIG. 17, and at the upper right as shown in FIG. 18.

Figure 19:
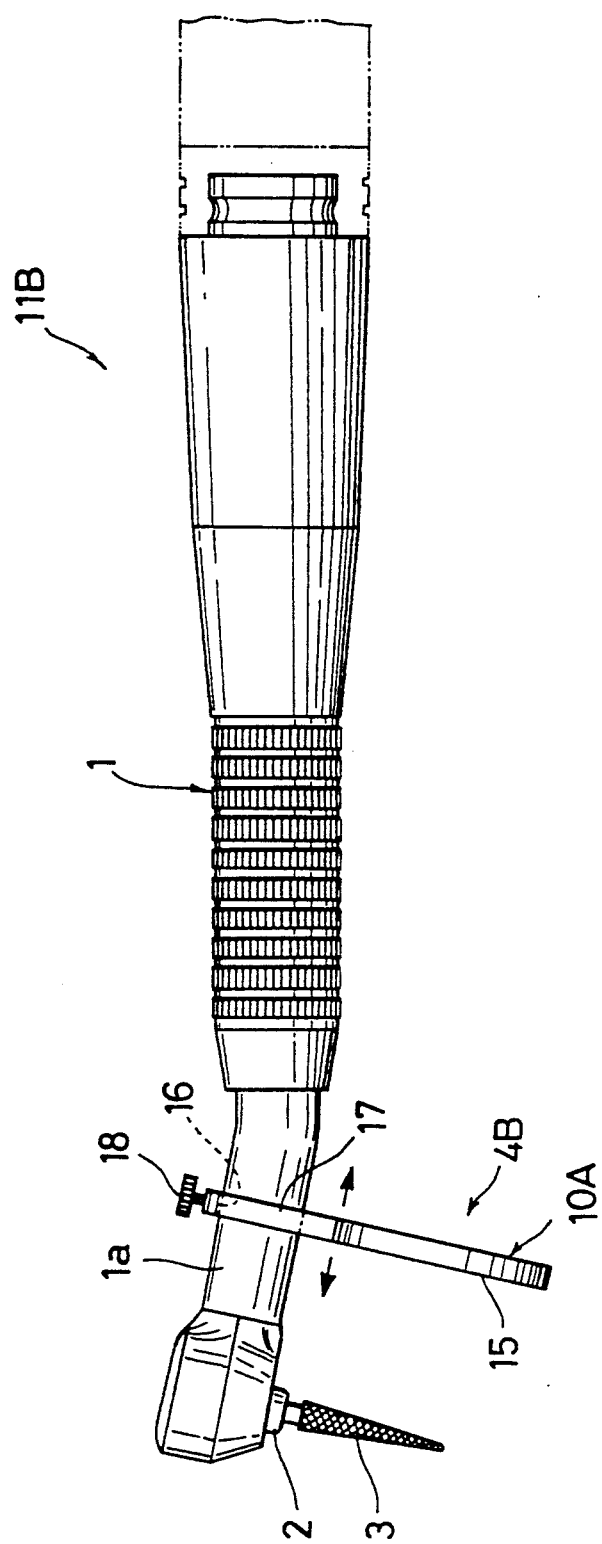
FIGS. 19 to 21 are explanatory views showing a third embodiment of the present invention.
Figure 20:
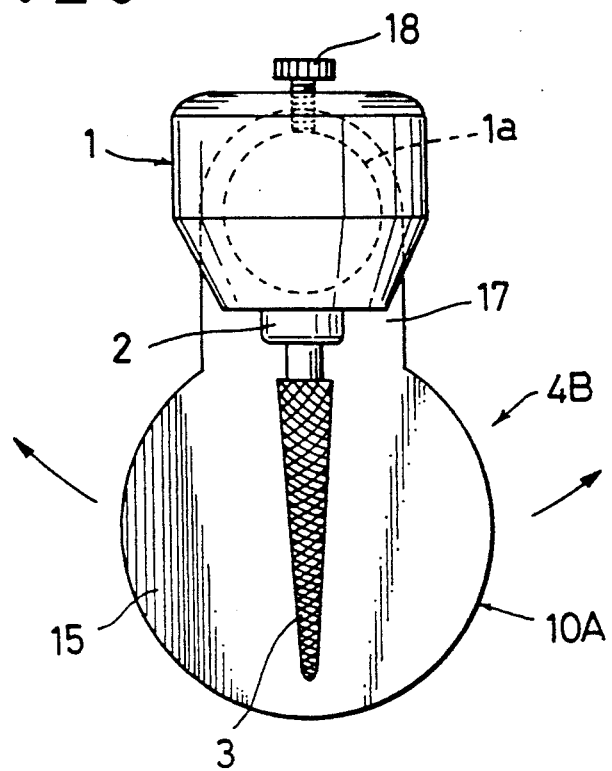
Figure 21:
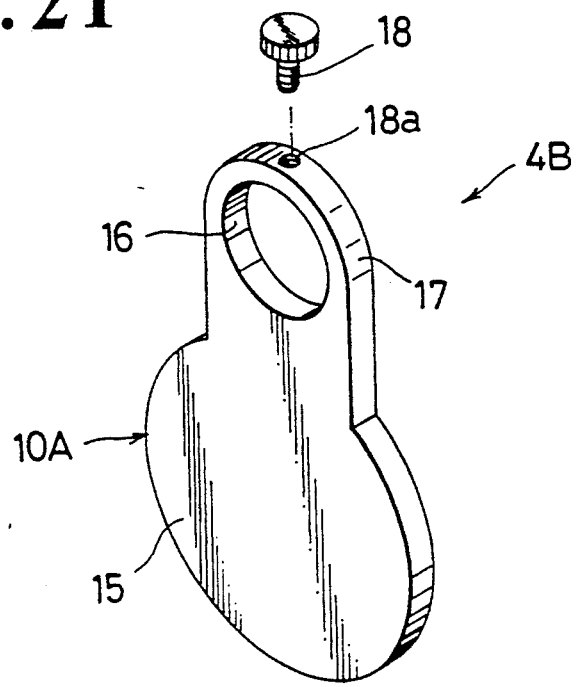

A third embodiment of the present invention shown in FIGS. 19 to 21 differs from the first embodiment by the fact that the guard device 4 is replaced with a modified guard device 4B which is mounted to a forward extension 1a of the dental tool body 1 for rotating and sliding movement. The guard device 4B comprises a guard plate 10A which is consisted of a disk-shaped holding tab 15 and a mounting portion 17 arranged integral with the holding tab 15 and having at center an opening 16 therein for fitting onto the forward extension 1a of the tool body 1, and a retaining screw 18 threaded into a thread hole 18a provided in the mounting portion 17 of the guard plate 10A for fastening the mounting portion 17 to the forward extension 1a of the tool body 1.

For assembling the guard device 4B with the dental tool body 1, the forward extension 1a of the tool body 1 is inserted into the opening 16 of the guard plate 10A prior to coupling to a head 2.

A dental tool 11B of the third embodiment thus becomes adjustable with the guide plate 10A which has been rotated and slid to a desired position and tightened by the screw 18.

Figure 22:
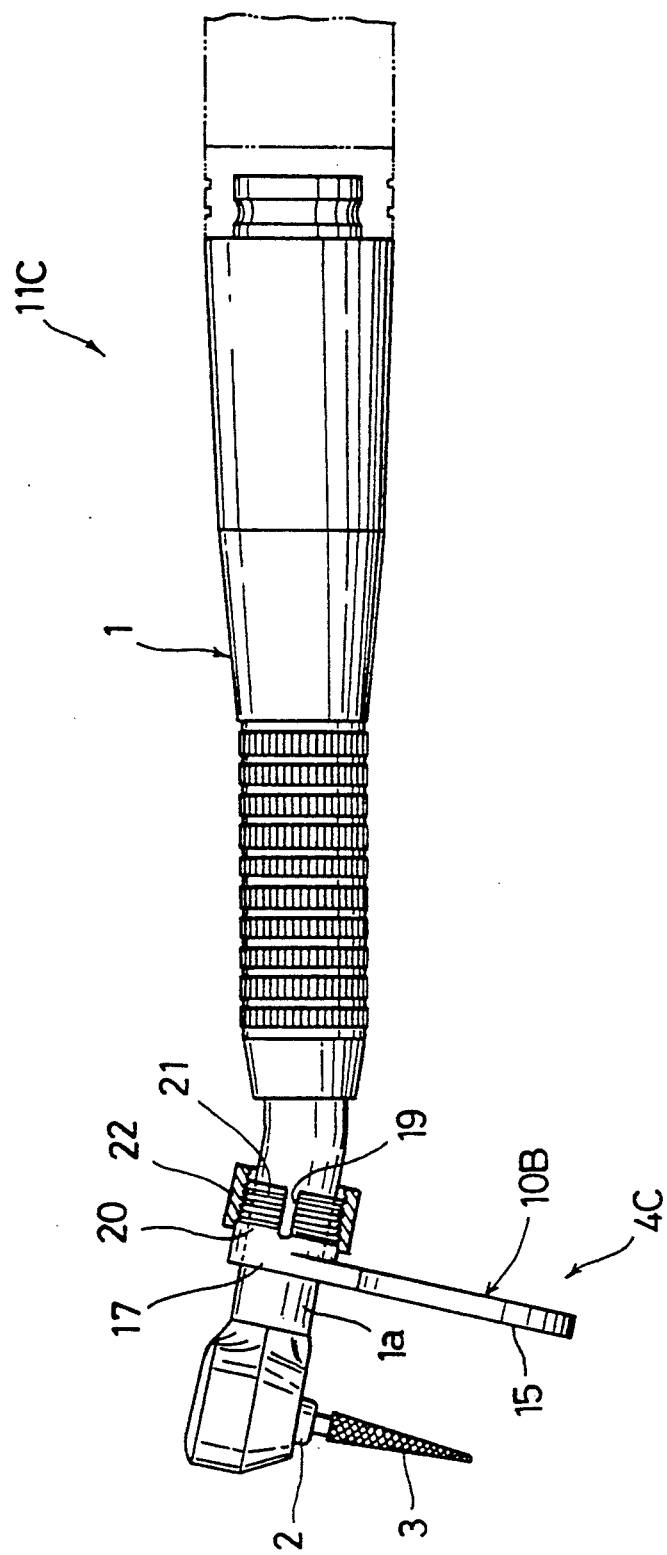
FIGS. 22 and 23 are explanatory views showing a fourth embodiment of the present invention.
Figure 23:
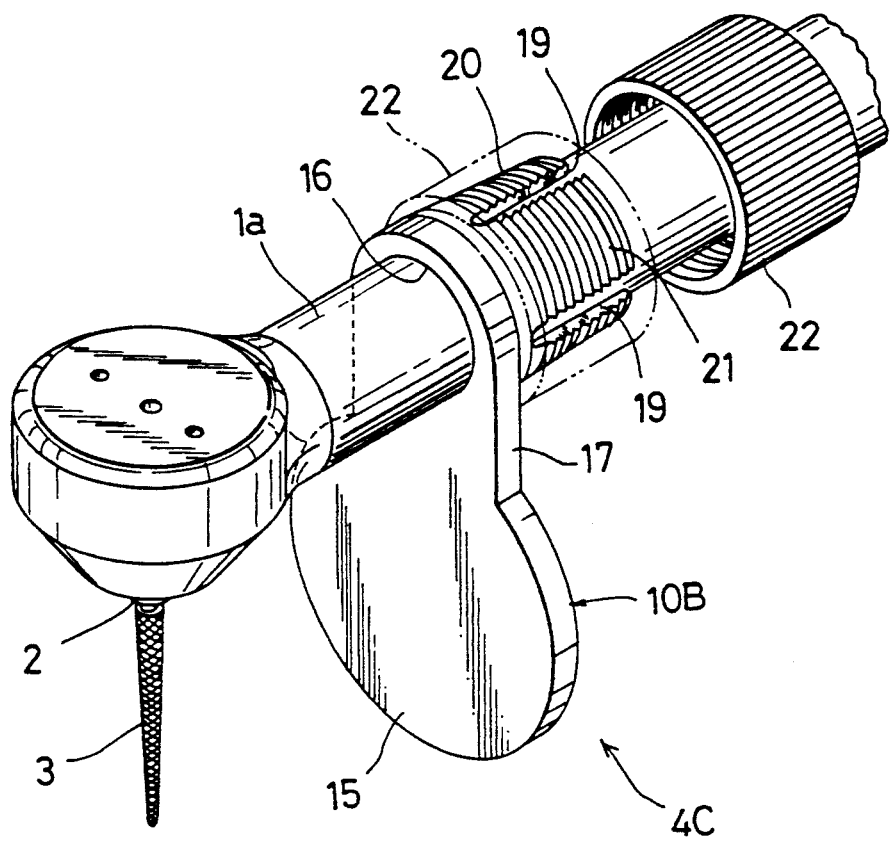

A fourth embodiment of the present invention shown in FIGS. 22 and 23 differs from the first embodiment by the fact that the guard device 4 is replaced with a modified guard device 4C which comprises a guard plate 10B consisting of a disk-shaped holding tab 15, a mounting portion 17, and a tubular thread 20 arranged integrally with the mounting portion 17 and having a plurality of lengthwise slits 19 therein and a tapered thread surface 21, the guard plate 10B has a retaining nut 22 threaded onto the thread surface 21 of the guard plate 10B so that the guard plate 10B can be tightened to the extension 1a of the dental tool body 1 as the tubular thread 20 remaining urged inwardly. A dental tool 11C equipped with the guard device 4C will provide the same effects as the third embodiment.

Figure 24:
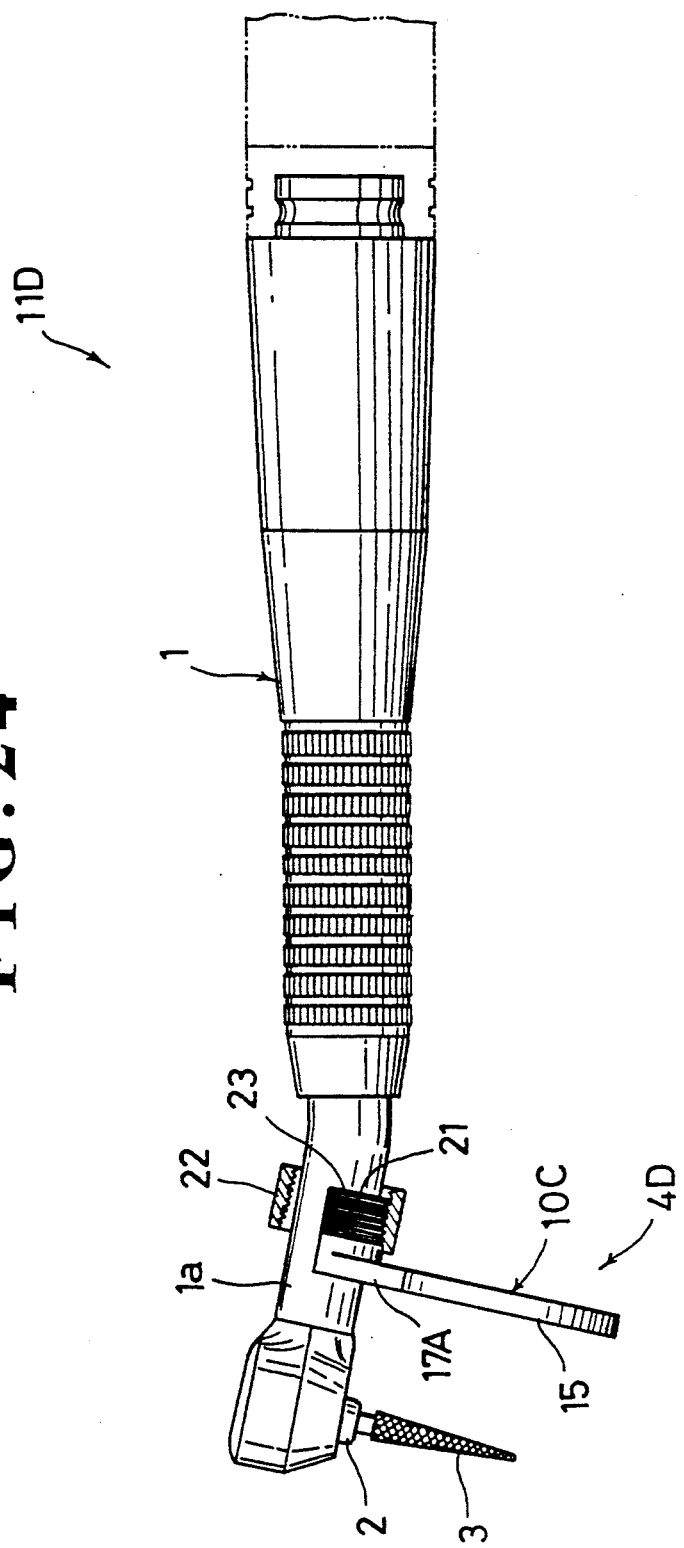
FIGS. 24 to 26 are explanatory views showing a fifth embodiment of the present invention.
Figure 25:
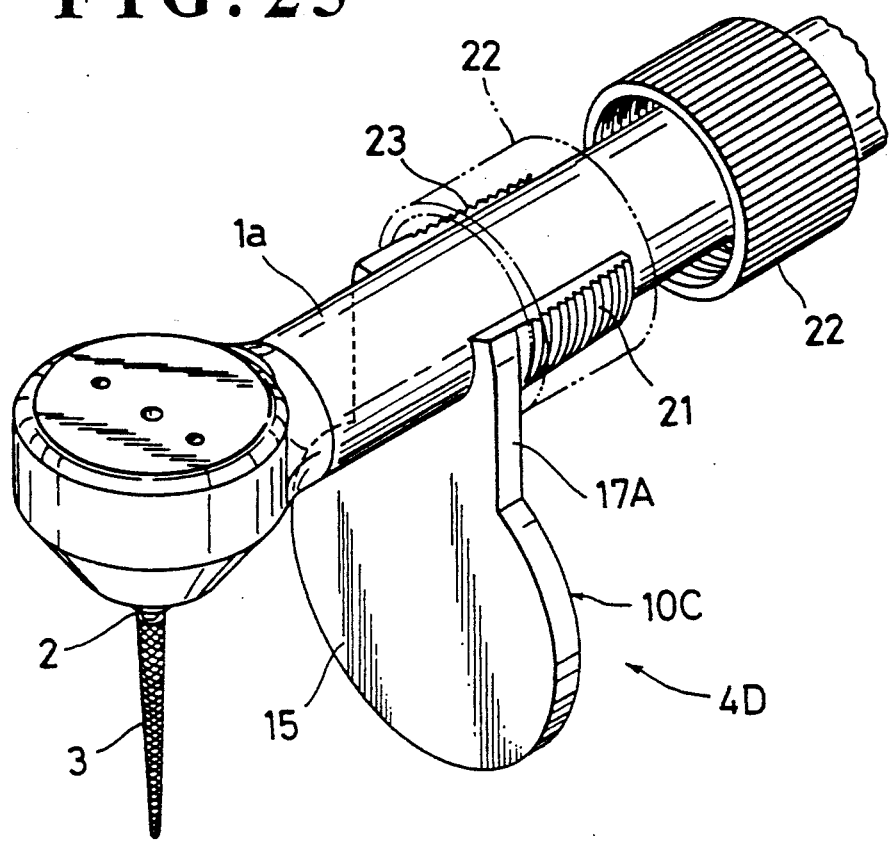
Figure 26:
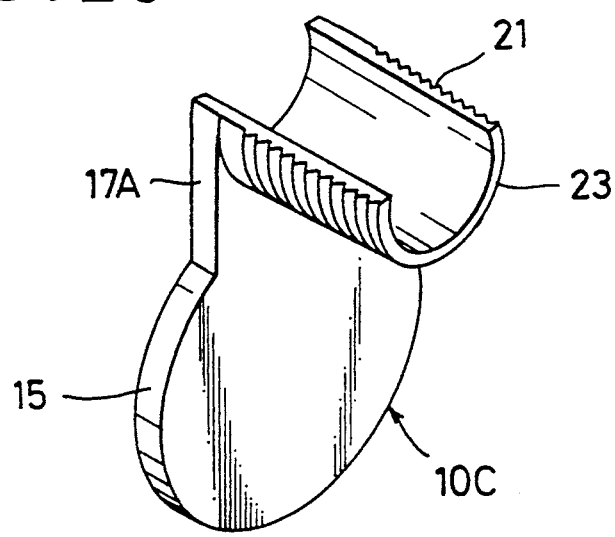

A fifth embodiment of the present invention shown in FIGS. 24 to 26 differs from the fourth embodiment by the fact that the guard device 4C is replaced with a modified guard device 4D which comprises a guard plate 10C consisting of a disk-shaped holding tab 15, a mounting portion 17A having a semi-circular notch therein, and a half-tubular thread 23 arranged integrally with the mounting portion 17A and having a tapered thread surface 21 thereof, and a retaining screw 22.

Accordingly, a dental tool 11D provided with the guard device 4D allows the guard plate 10C to be dismounted with ease.

Figure 27:
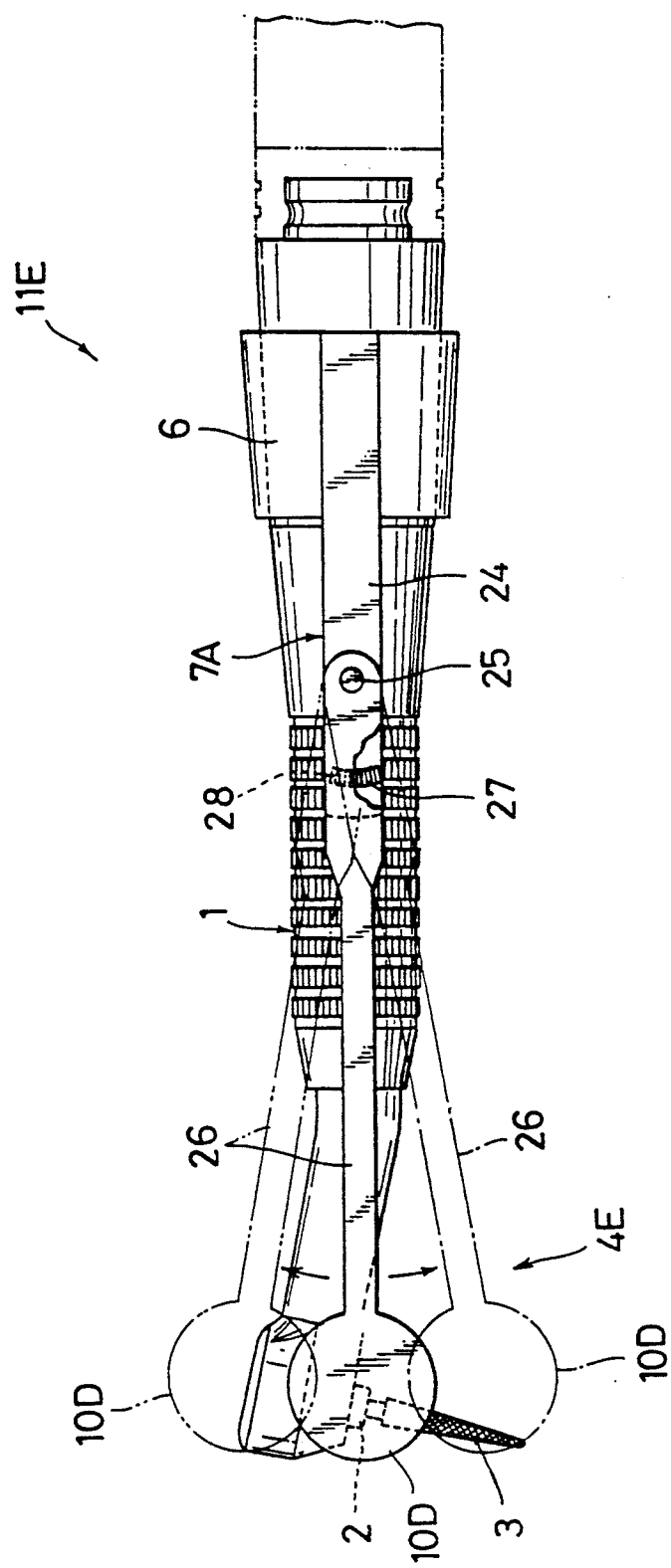
FIGS. 27 to 29 are explanatory views showing a sixth embodiment of the present invention.
Figure 28:
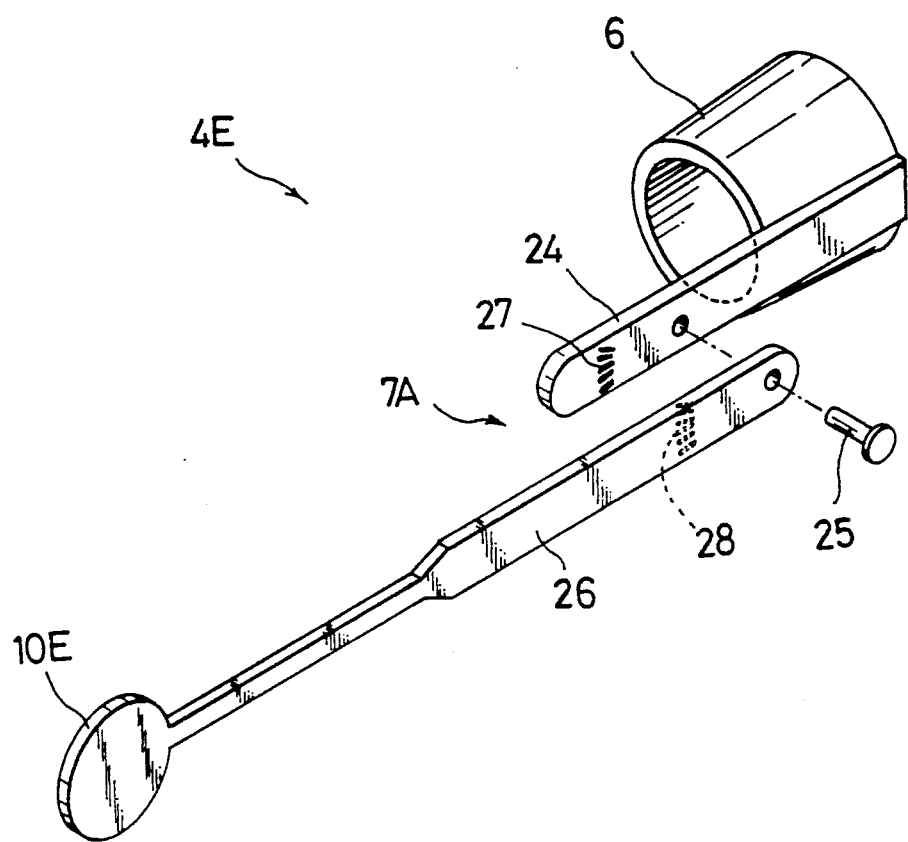
Figure 29:
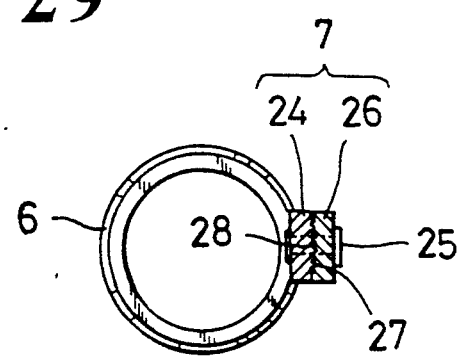

A sixth embodiment of the present invention shown in FIGS. 27 to 29 differs from the first embodiment by the fact that the guard device 4 is replaced with a modified guard device 4E in which an arm 7A comprises a stationary arm 24 fixedly mounted to the fitting ring 6, a movable arm 26 having its distal end a guard plate 10D, and a pin 25 by which the movable arm 26 is coupled to the distal end of the stationary arm 24 so that it can swing upward and downward about the pin 25. In particular, the stationary arm 24 and the movable arm 26 have sets of serrations 27 and 28 respectively provided on the corresponding surfaces thereof and are coupled to each other by a considerable strength of the pin 25. Accordingly, the movable arm 26 remains stationary at an angle or linear to the stationary arm 24 in a normal state and can pivotably be moved about the pin 25 by an outside force.

A dental tool 11E provided with the guard device 4E having the arm 7A can be used with the guard plate 10D arranged at a desired vertical position.

Figure 30:
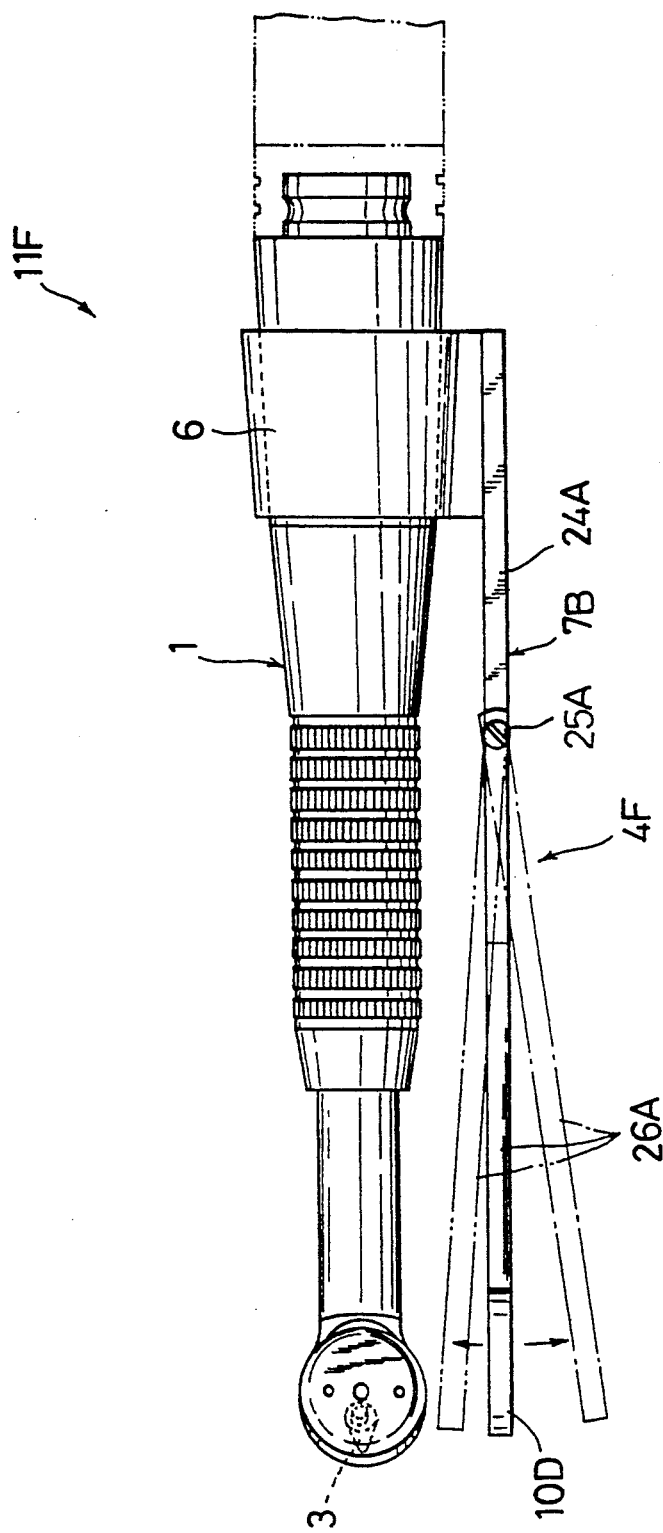
FIGS. 30 and 31 are explanatory views showing a seventh embodiment of the present invention.
Figure 31:
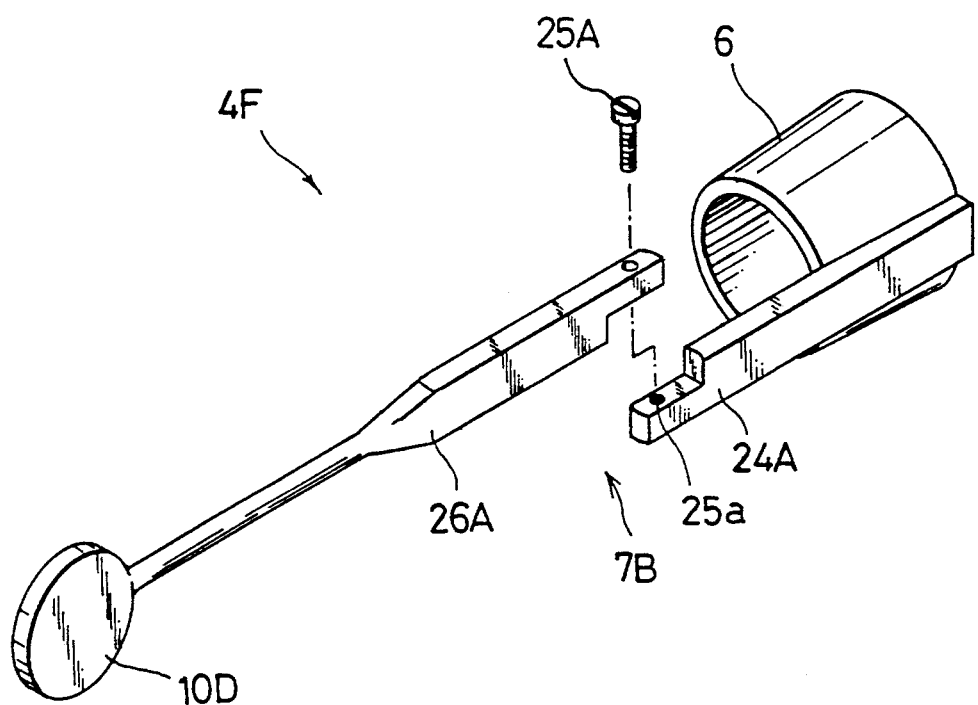
Figure 32:
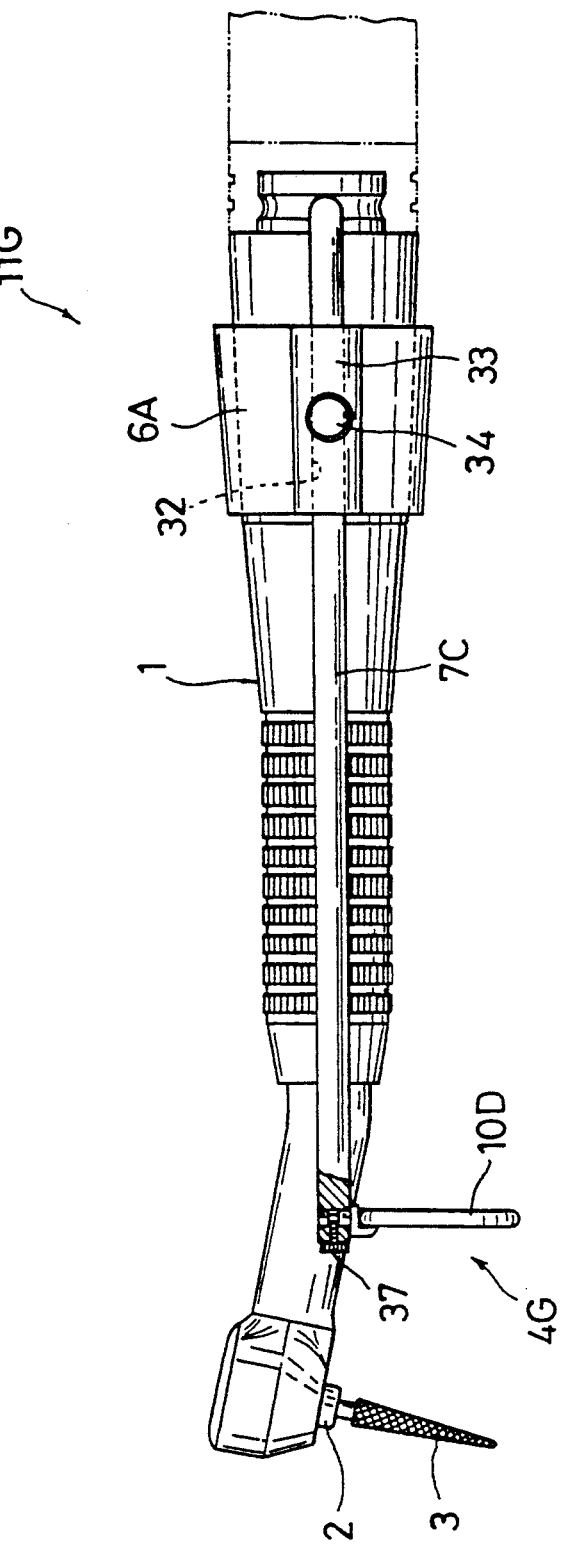
FIGS. 32 to 35 are explanatory views showing an eighth embodiment of the present invention.
Figure 33:
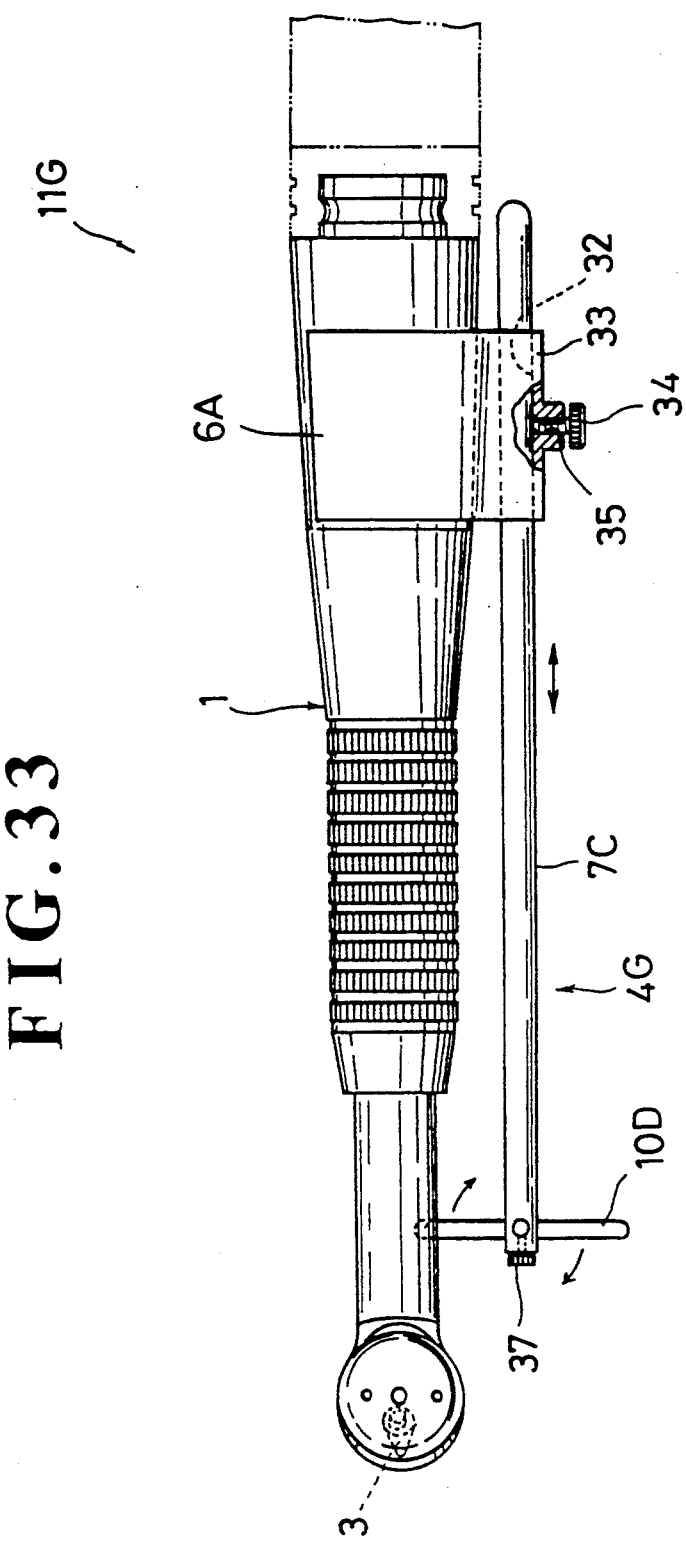
Figure 34:
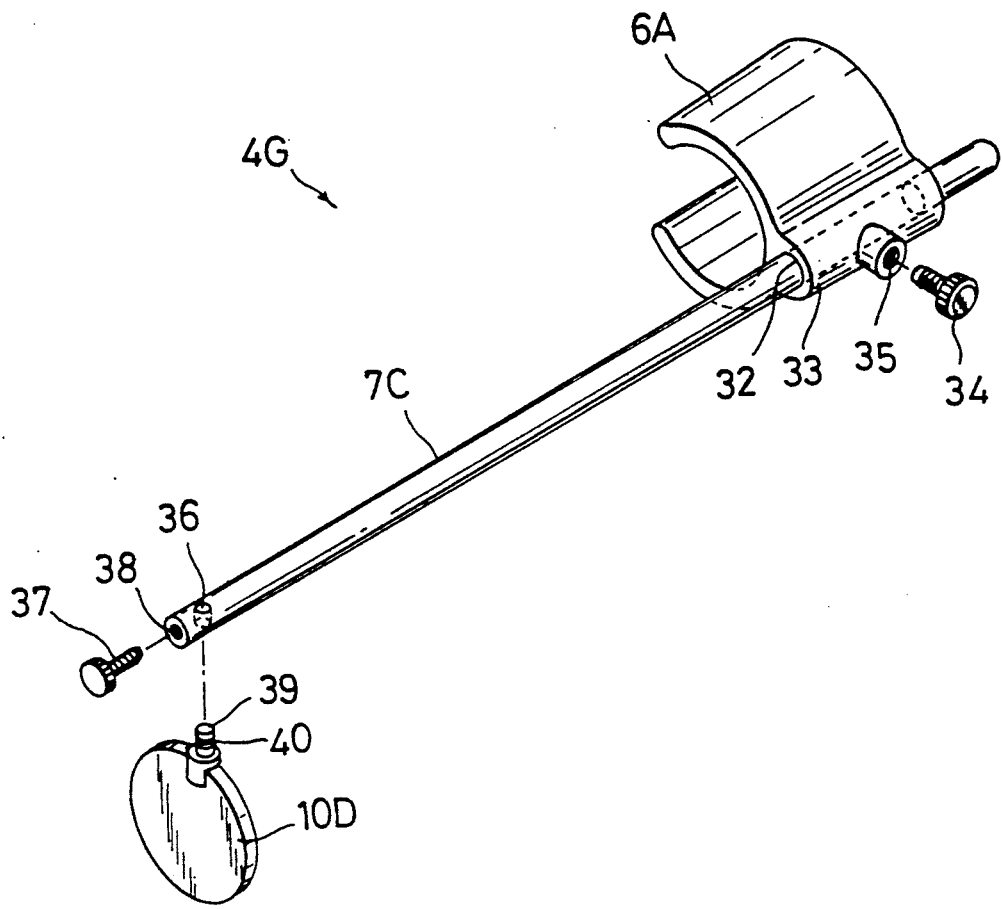
Figure 35:
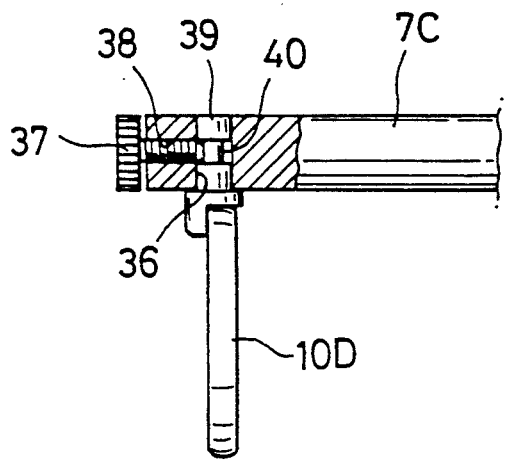

A seventh embodiment of the present invention shown in FIGS. 30 and 31 differs from the first embodiment by the fact that the guard device 4 is replaced with a modified guard device 4F in which an arm 7B comprises a stationary arm 24A fixedly mounted to the fitting ring 6, a movable arm 26A having at its distal end a guard plate 10D, and a screw 25A threaded through a hole of the movable arm 26A into a female thread 25a provided in the distal end of the stationary arm 24A so that the movable arm 26A can swing leftward and rightward about the screw 25A.

Accordingly, a dental tool 11F provided with the guard device 4F having the arm 7B can be used with the guard plate 10D fastened at a desired horizontal position.

An eighth embodiment of the present invention shown in FIGS. 32 to 35 is differs from the first embodiment by the fact that the guard device 4 is replaced with a modified guard device 4G in which an arm 7C is slidably fitted at its proximal end into the through hole 32 of an arm support portion 33 of a C-shaped fitting member 6A so that it can stay at a desired position with a retaining screw 34 tightened through a female thread 35 of the arm support portion 33 and has at its distal end a guard plate 10D. Accordingly, a dental tool 11G provided with the guard device 4G allows the arm 7C to extend or retract and the guard plate 10D to be rotated with the arm 7C for optimum positioning.

In more particular, the arm 7C has a thread hole 38 provided in the distal end thereof into which a guard plate retaining screw 37 is threaded, and a shaft hole 36 provided in the same to communicate with the thread hole 38. The guard plate 10D incorporates a shaft 39 which is fitted into the shaft hole 36 of the arm 7C. The shaft 39 has at its center a recess 40 for accepting the forward end of the guard plate retaining screw 37.

Figure 36:
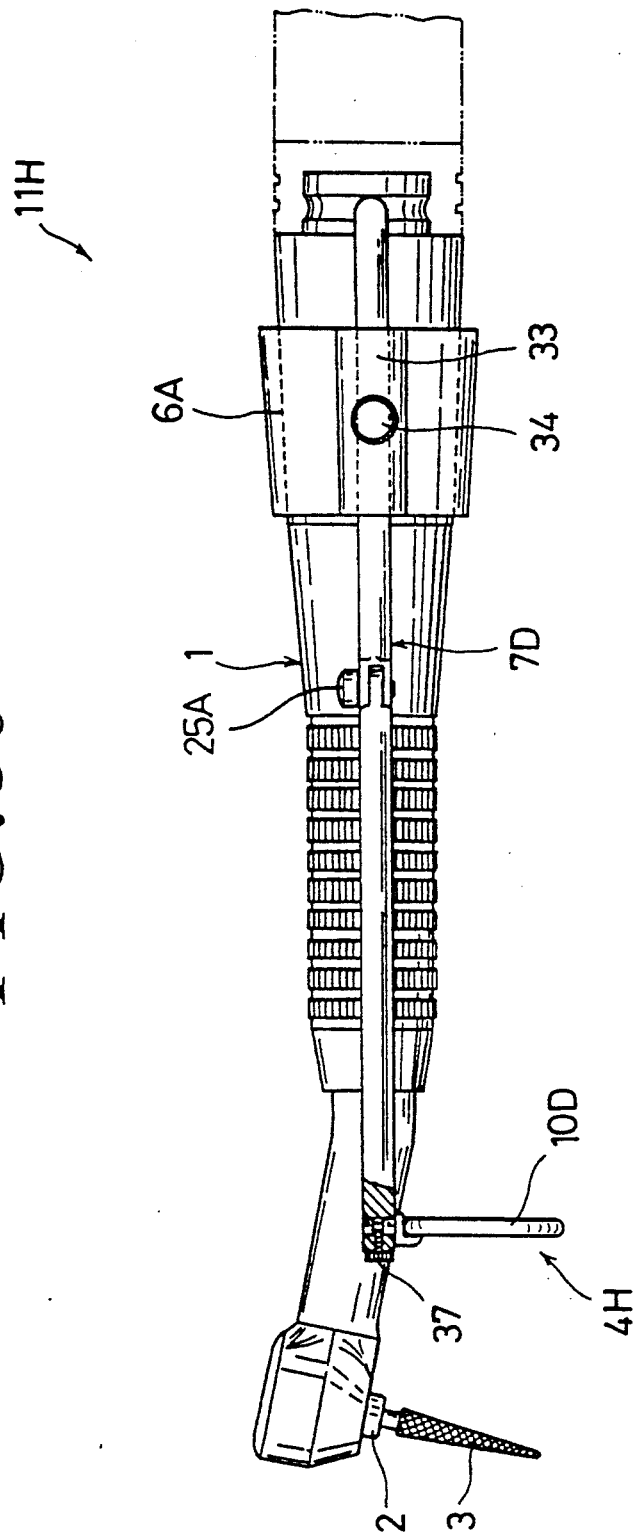
FIGS. 36 to 38 are explanatory views showing a ninth embodiment of the present invention.
Figure 37:
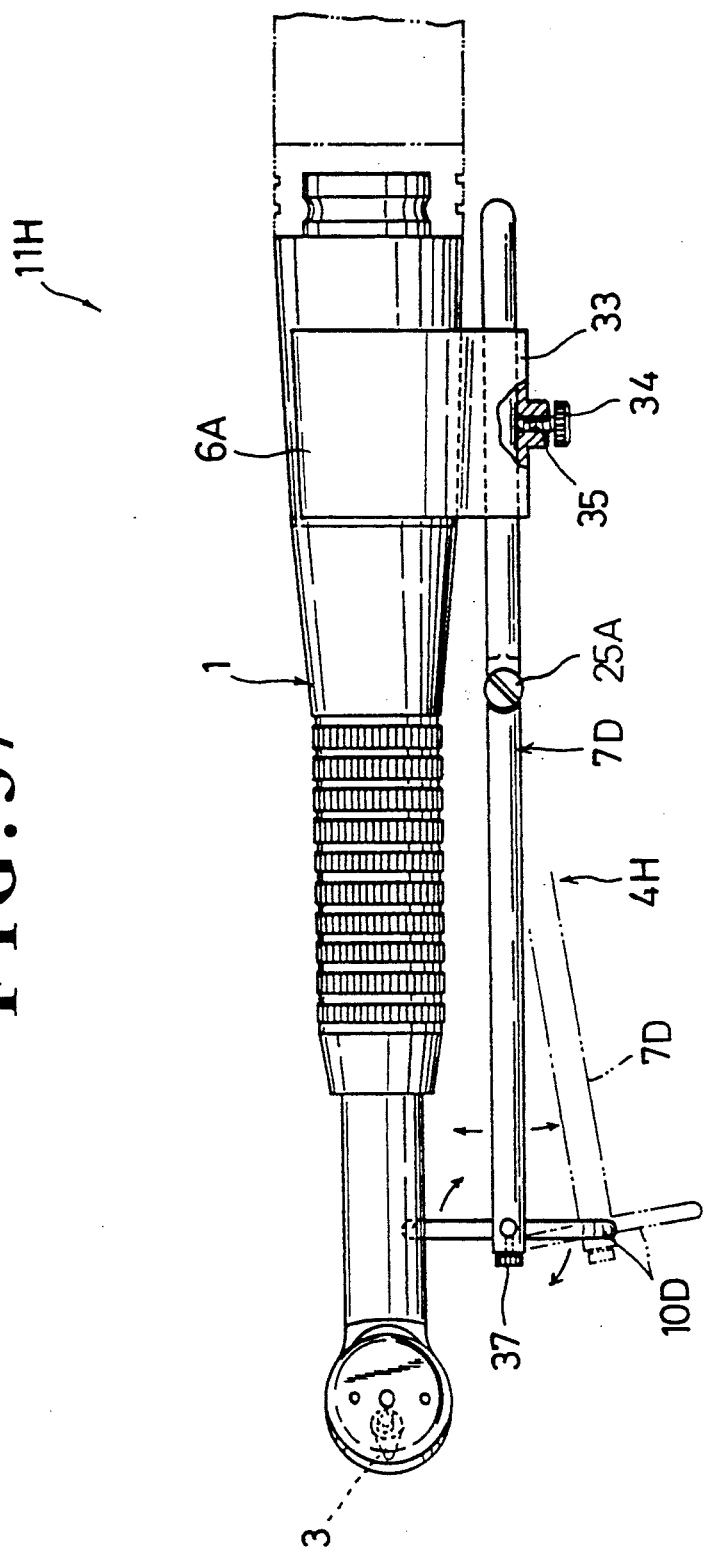
Figure 38:
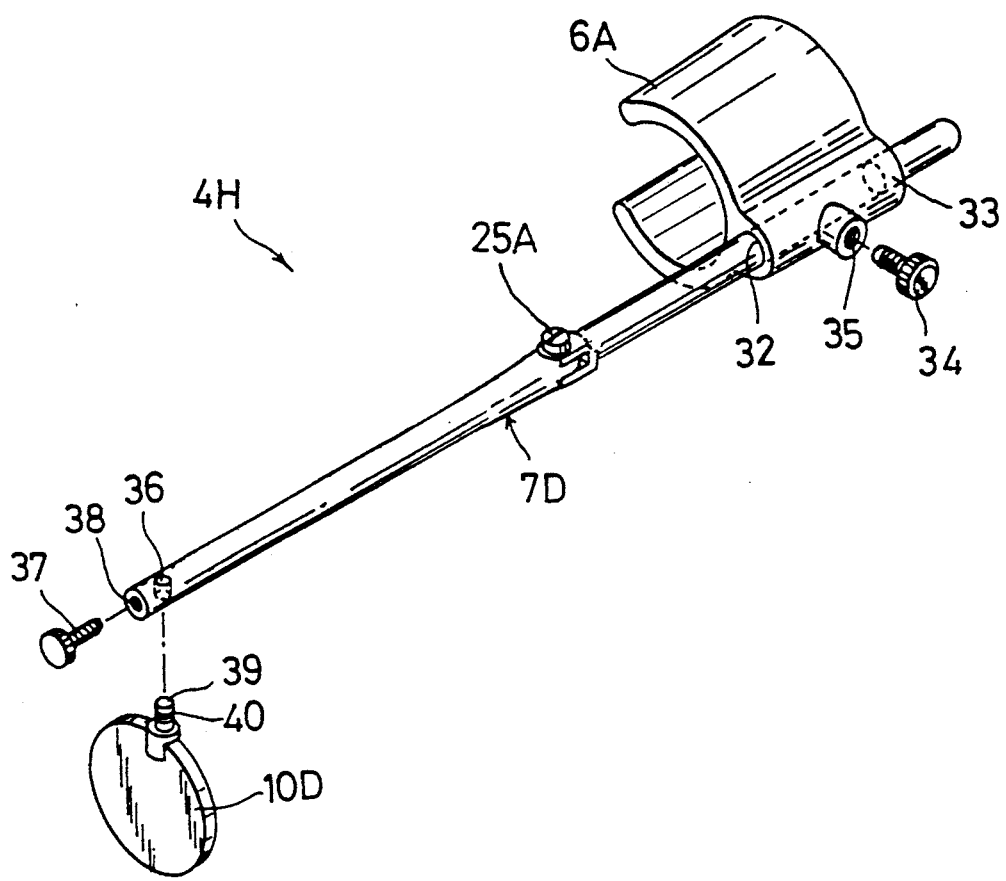

A ninth embodiment of the present invention shown in FIGS. 36 to 38 differs from the eighth embodiment by the fact that the guard device 4G is replaced with a modified guard device 4H in which an arm 7D is adapted to be foldable to the left or right. Accordingly, a dental tool 11H provided with the guard device 4H allows the arm 7D to extend or retract and turn to left or right, and the guard plate 10D to be rotated with the arm 7D for optimum positioning.

Figure 39:
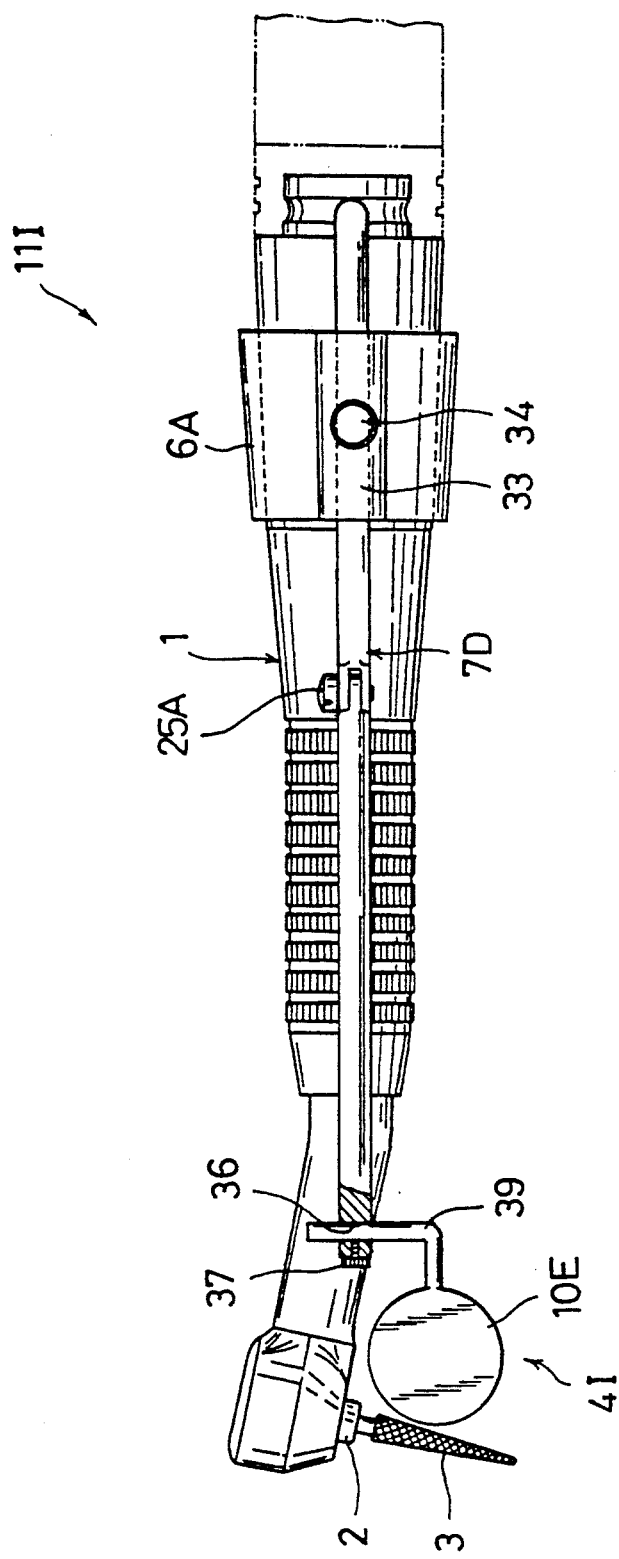
FIGS. 39 to 41 are explanatory views showing a tenth embodiment of the present invention.
Figure 40:
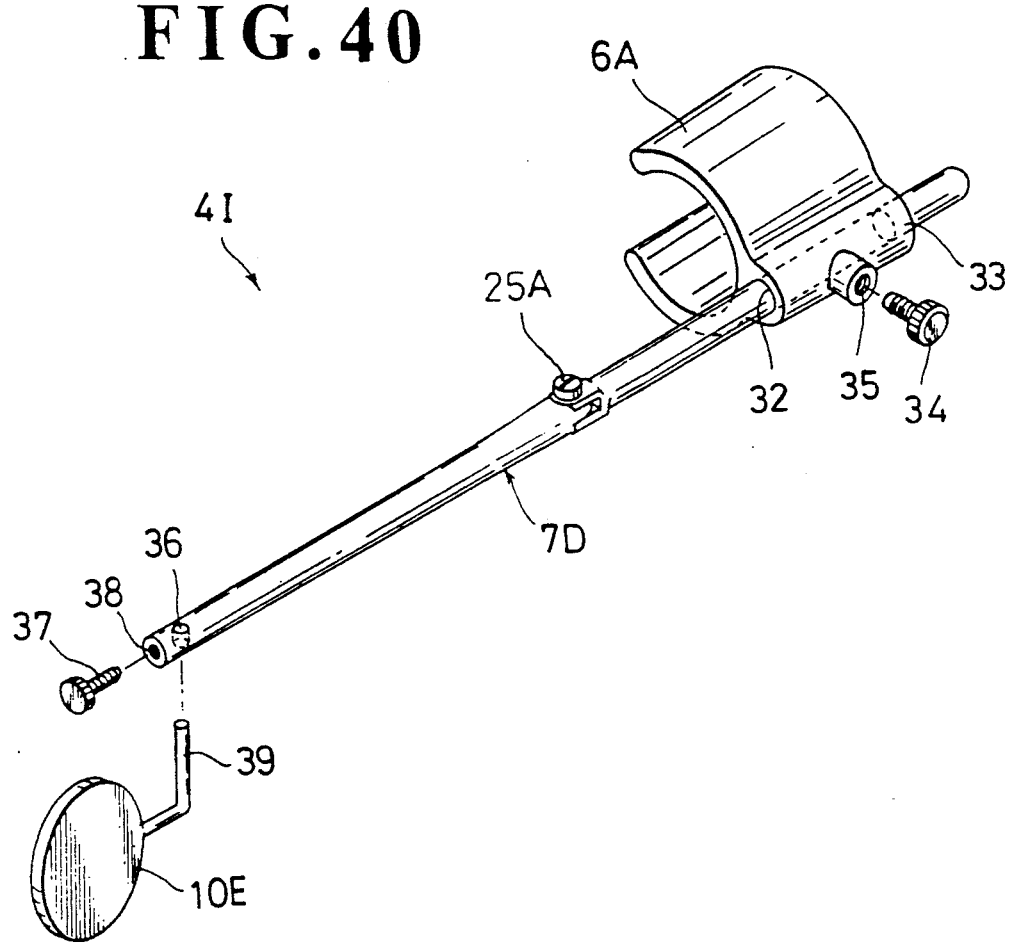
Figure 41:
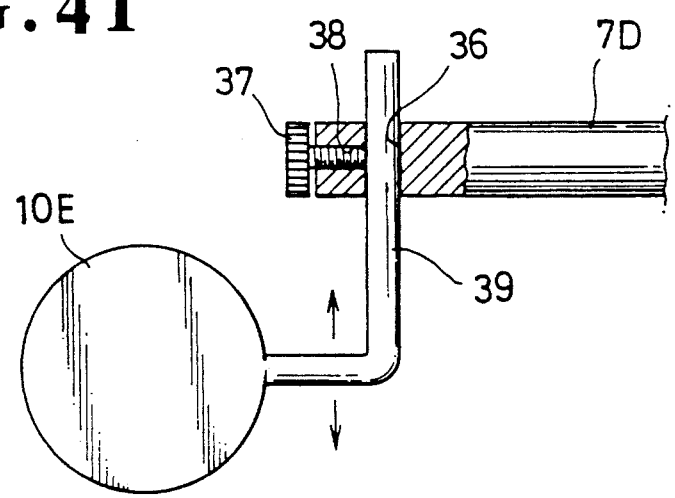

A tenth embodiment of the present invention shown in FIGS. 39 to 41 differs from the ninth embodiment by the fact that the guard device 4H is replaced with a modified guard device 4I in which a guard plate 10E has an L-shaped shaft 39 thereof which is fixedly fitted into the shaft hole 36 of the arm 7D. Accordingly, a dental tool 11I provided with the guard device 4I allows the guard plate 10E to be rotated with the arm 7D and also, moved upward and downward to a desired position.

Figure 42:
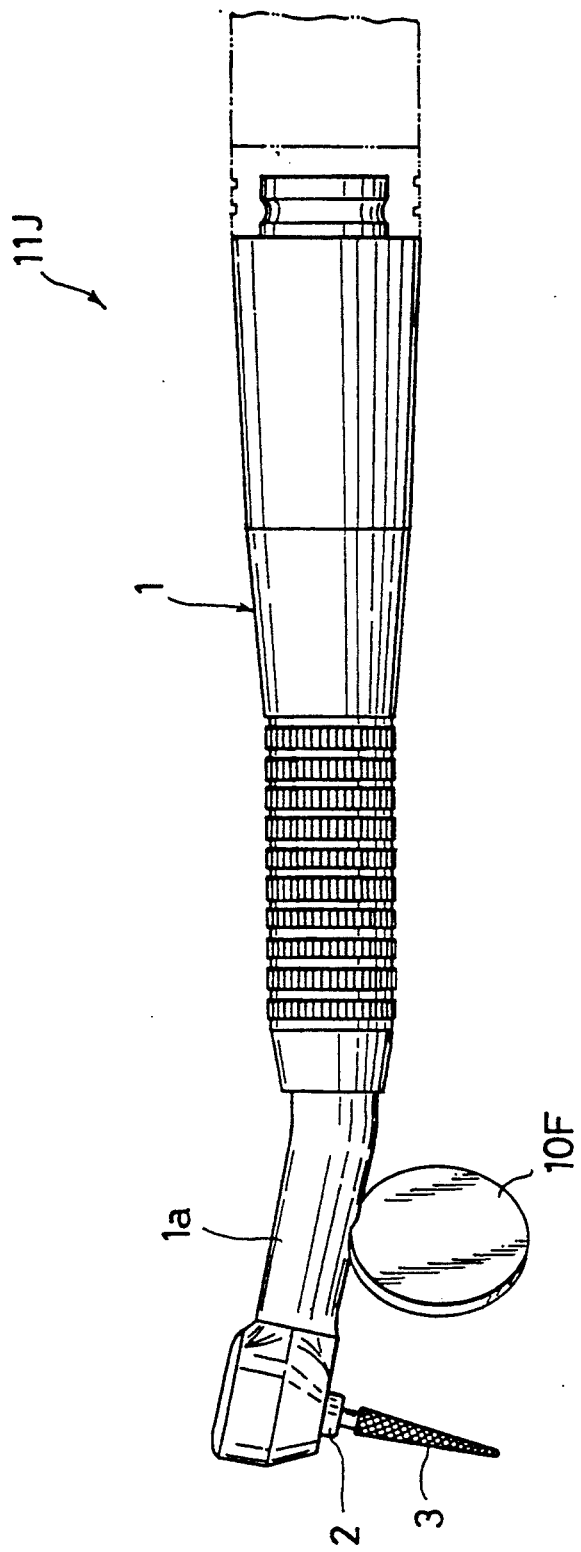
FIGS. 42 to 45 are explanatory views showing an eleventh embodiment of the present invention.
Figure 43:
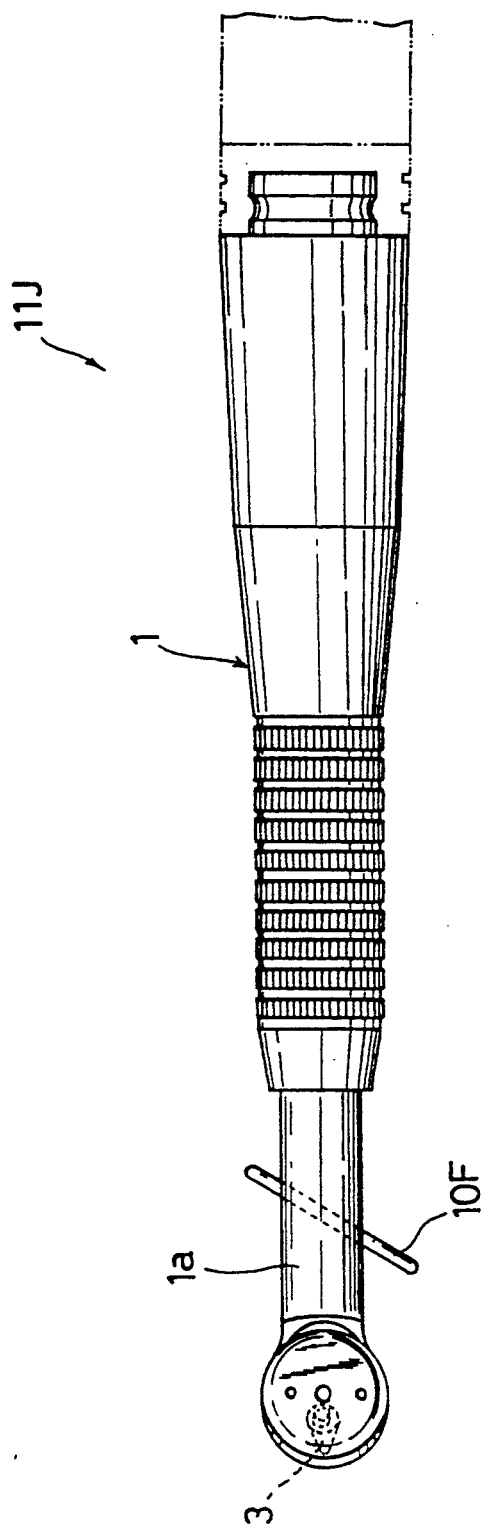
Figure 44:
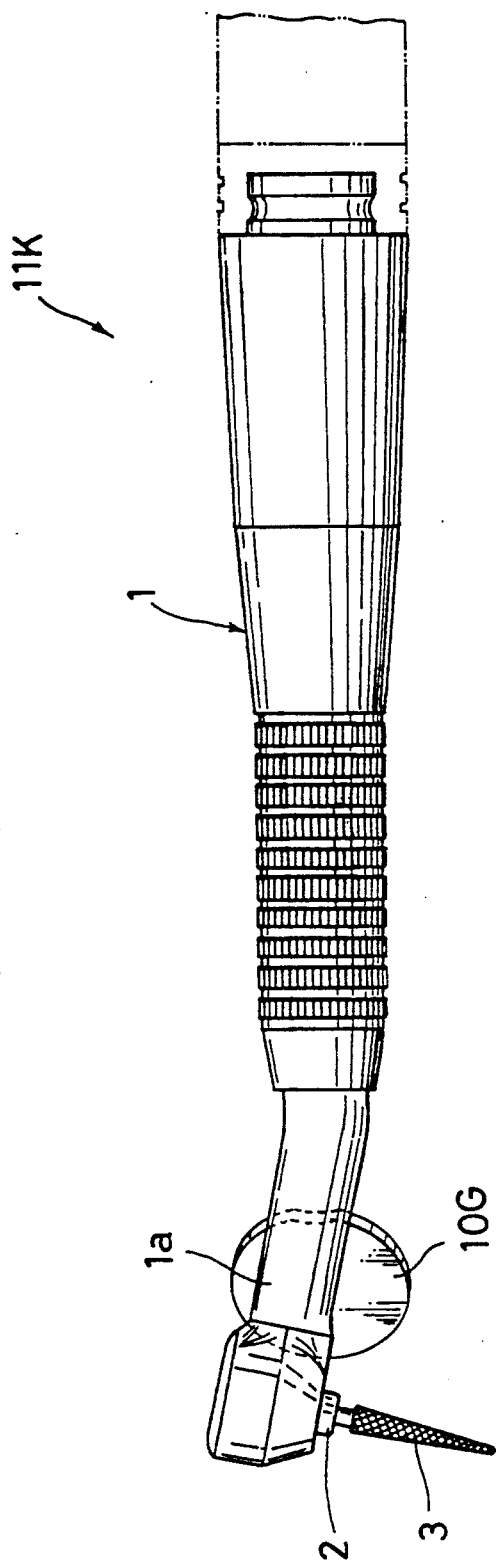
Figure 45:
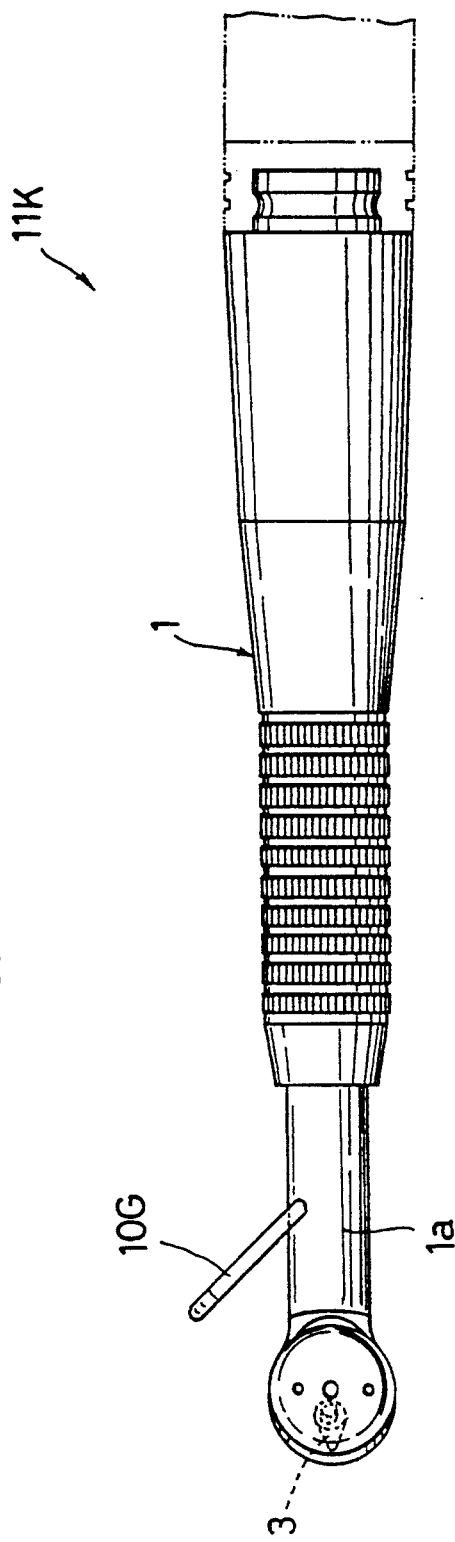

An eleventh embodiment of the present invention shown in FIGS. 42 to 45 differs from the first embodiment by the fact that a guard plate 10F is fixedly mounted at an angle to the forward extension 1a of the tool body 1, as shown in FIGS. 42 and 43, so that a dental tool 11J can successfully be used for treatment on a decayed tooth at both the lower left and the lower right of the dentition. Also, as shown in FIGS. 44 and 45, a guard plate 10G is fixedly mounted at an angle to a different location of the forward portion 1a of the tool body 1 so that a resultant dental tool 11K can be used for treatment on a decayed tooth at both the upper left and the upper right. Accordingly, the eleventh embodiment will provide the same effects as of the first embodiment.

Figure 46:
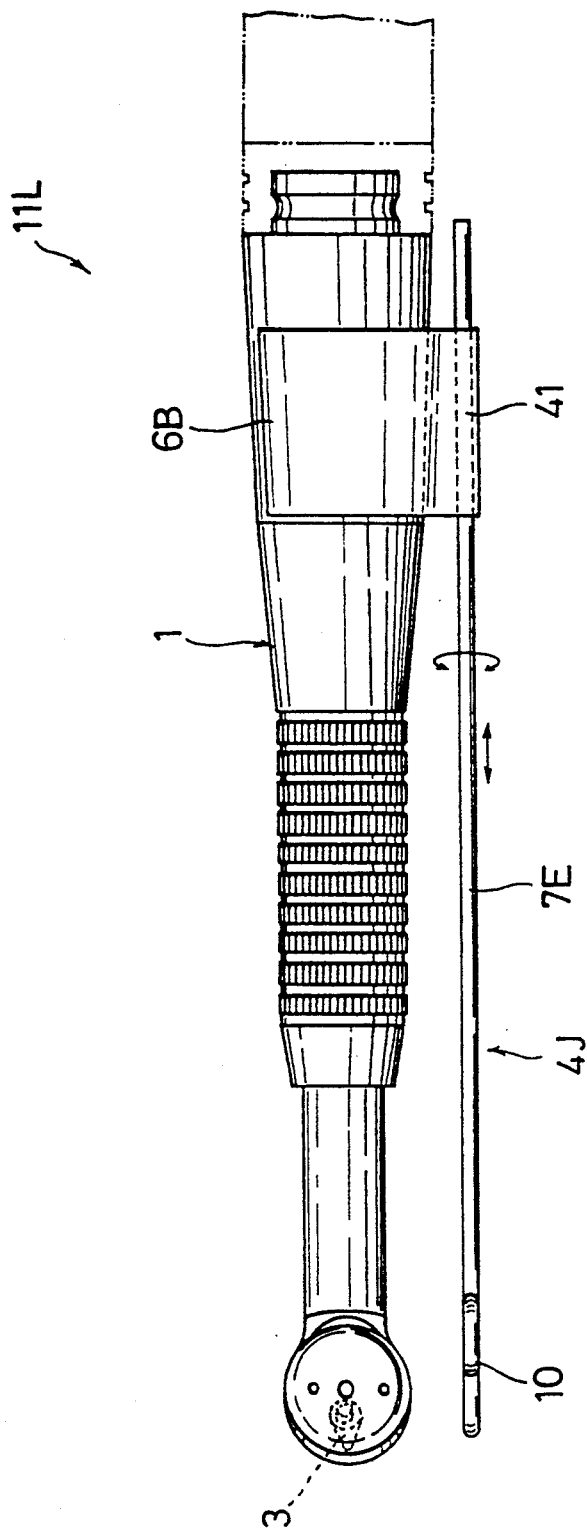
FIGS. 46 and 47 are explanatory views showing a twelfth embodiment of the present invention.
Figure 47:
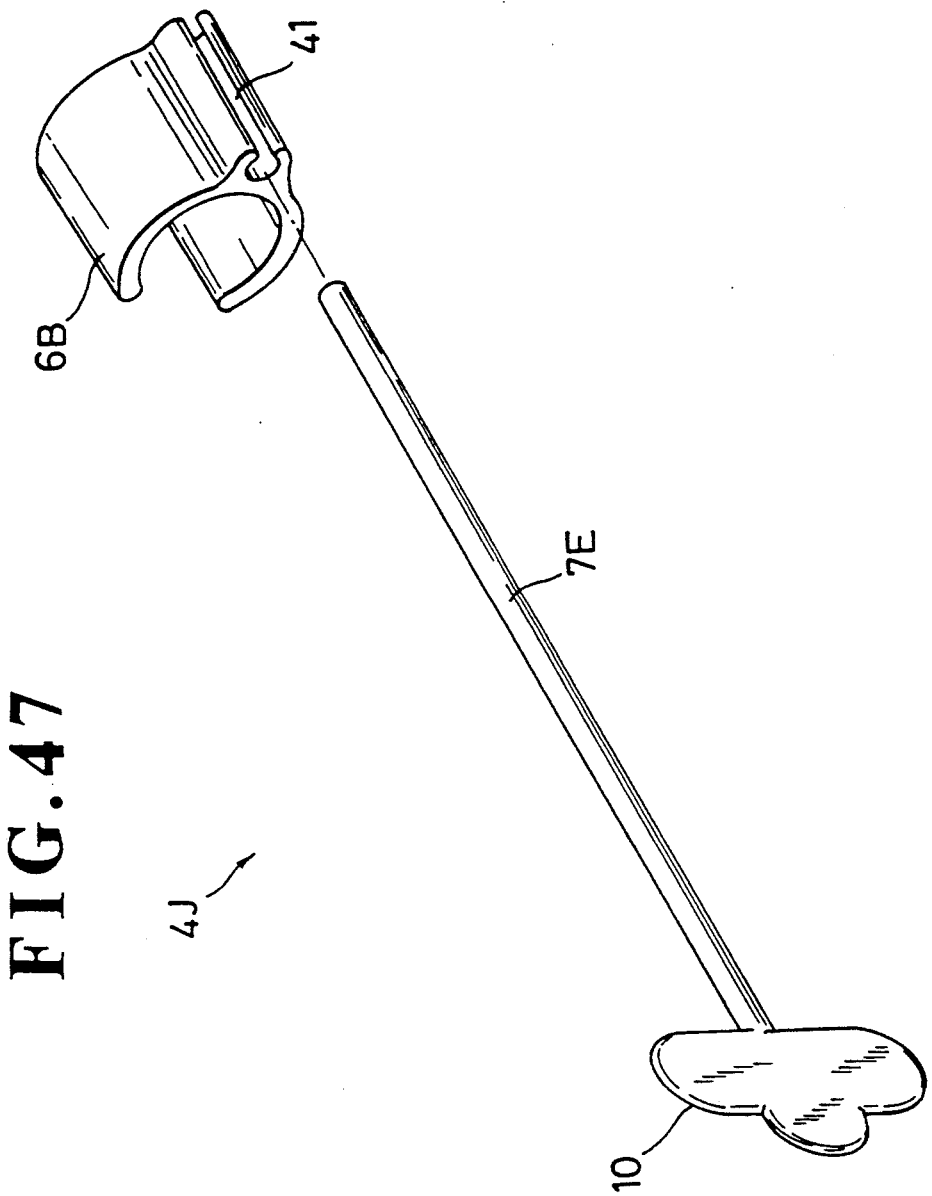

A twelfth embodiment of the present invention shown in FIGS. 46 and 47 differs from the first embodiment by the fact that the guard device 4 is replaced with a modified guard device 4J in which an arm 7E is supported by an arm support 41 provided on the outer surface of a C-shaped fitting member 6B which is made of a synthetic resin material and detachably mounted to the tool body 1. Accordingly, a dental tool 11L provided with the guard device 4J allows the arm 7E to extend or retract and rotate for optimum positioning.

Figure 48:
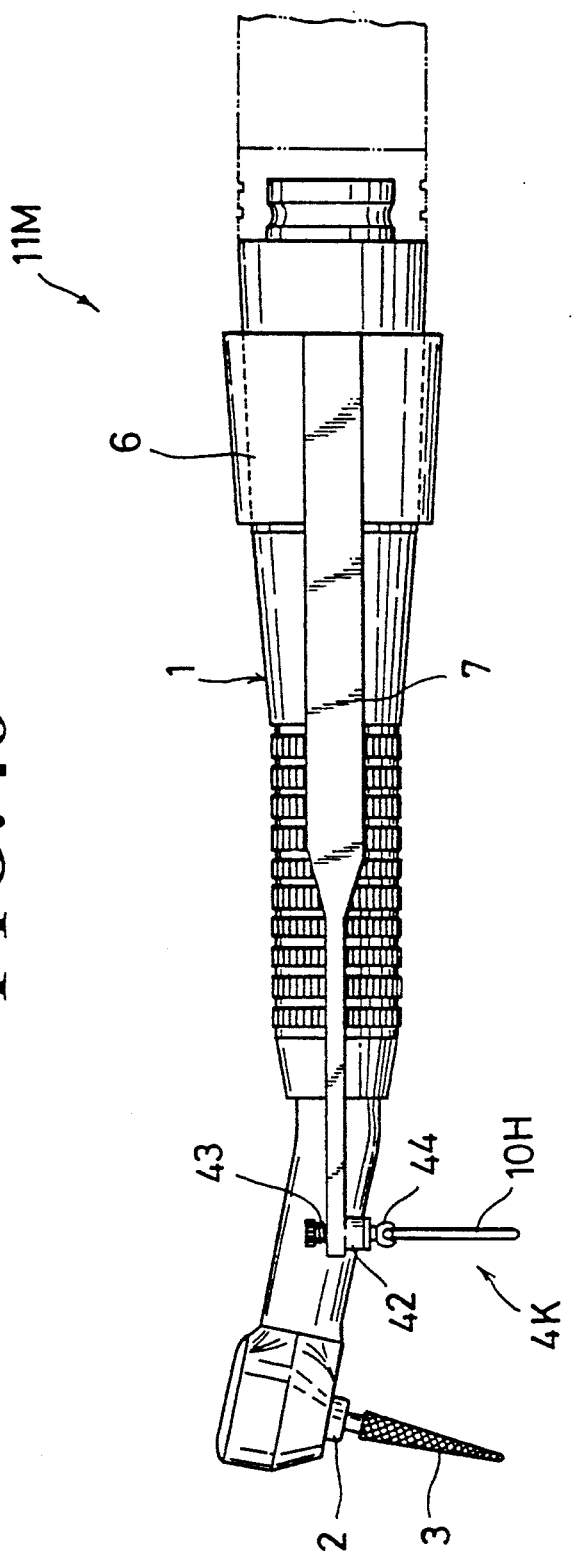
FIGS. 48 to 50 are explanatory views showing a thirteenth embodiment of the present invention.
Figure 49:
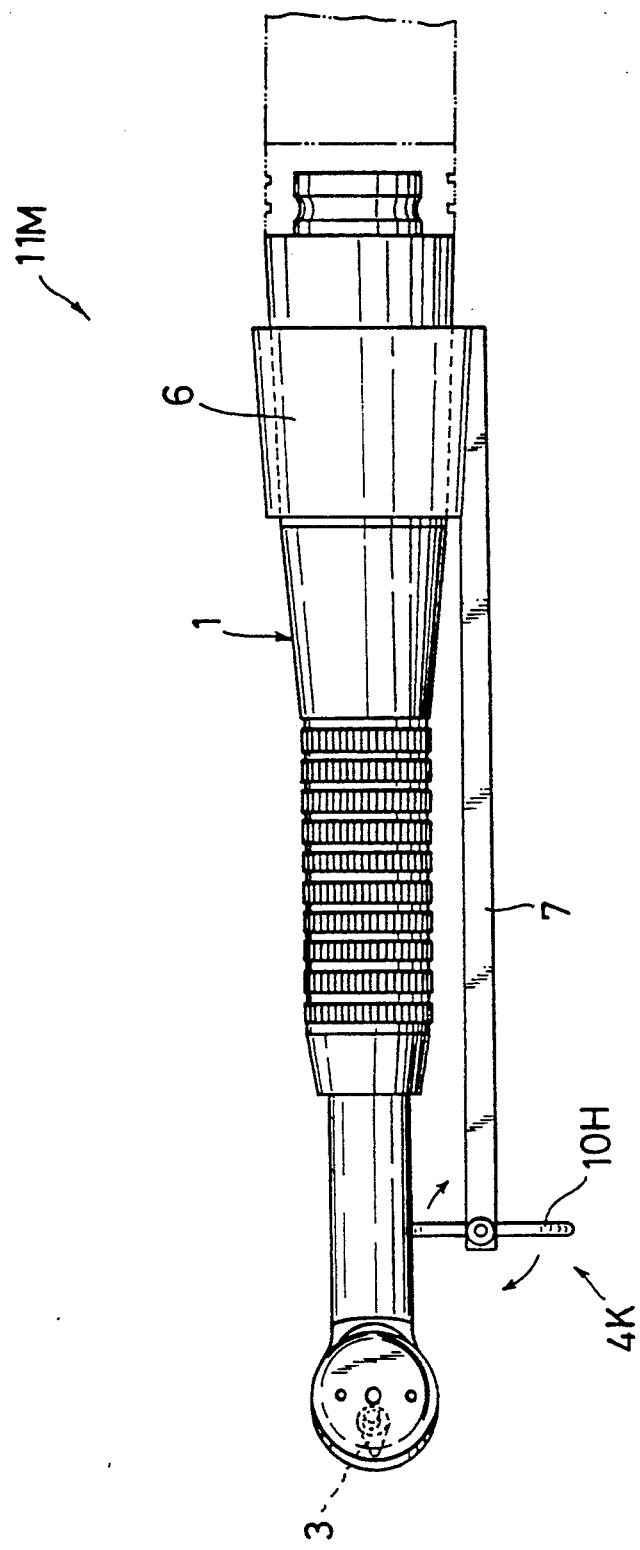
Figure 50:
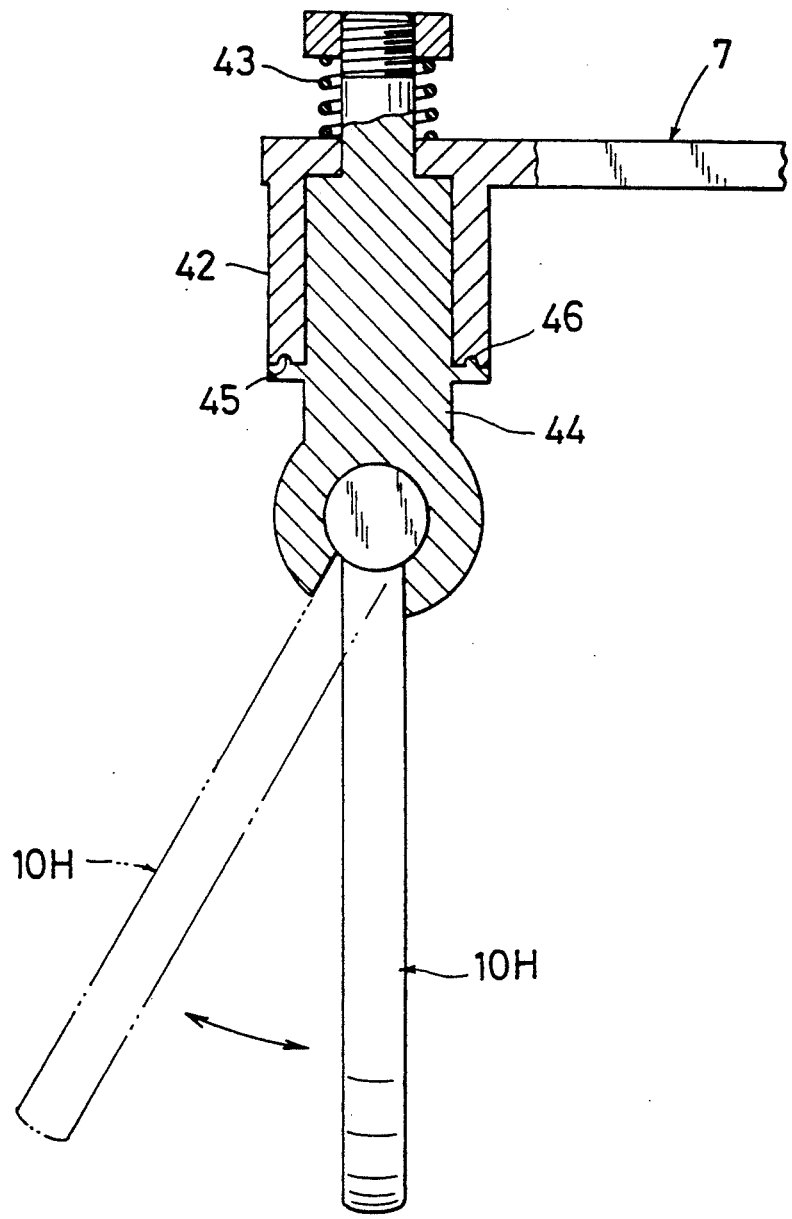

A thirteenth embodiment of the present invention shown in FIGS. 48 to 50 differs from the first embodiment by the fact that the guard device 4 is replaced with a modified guard device 4K in which the arm 7 has a shaft holder 42 provided integrally on the distal end thereof for holding a shaft 44 of a guard plate 10H which remains urged by a spring 43 in a locking direction. The guard plate 10H is arranged tiltable to a given angle. A dental tool 11M provided with the guard device 4K will be operated with equal success.

In particular, the shaft holder 42 of a tubular shape has a plurality of recesses 45 in the lower opening end wall thereof. Also, a corresponding number of projections 46 are provided on a rib flange of the guard plate shaft 44 for engagement with the recesses 45 of the shaft holder 42. Accordingly, the guard plate shaft 44 can be set at a desired position to the shaft holder 42 by pulling against the yielding force of the spring 43 for disengagement of its projections 46 from the recesses 45 of the shaft holder 42 and after turning to the desired position, allowing the projections 46 to fit back into the recess 45 for locking.

Figure 51:
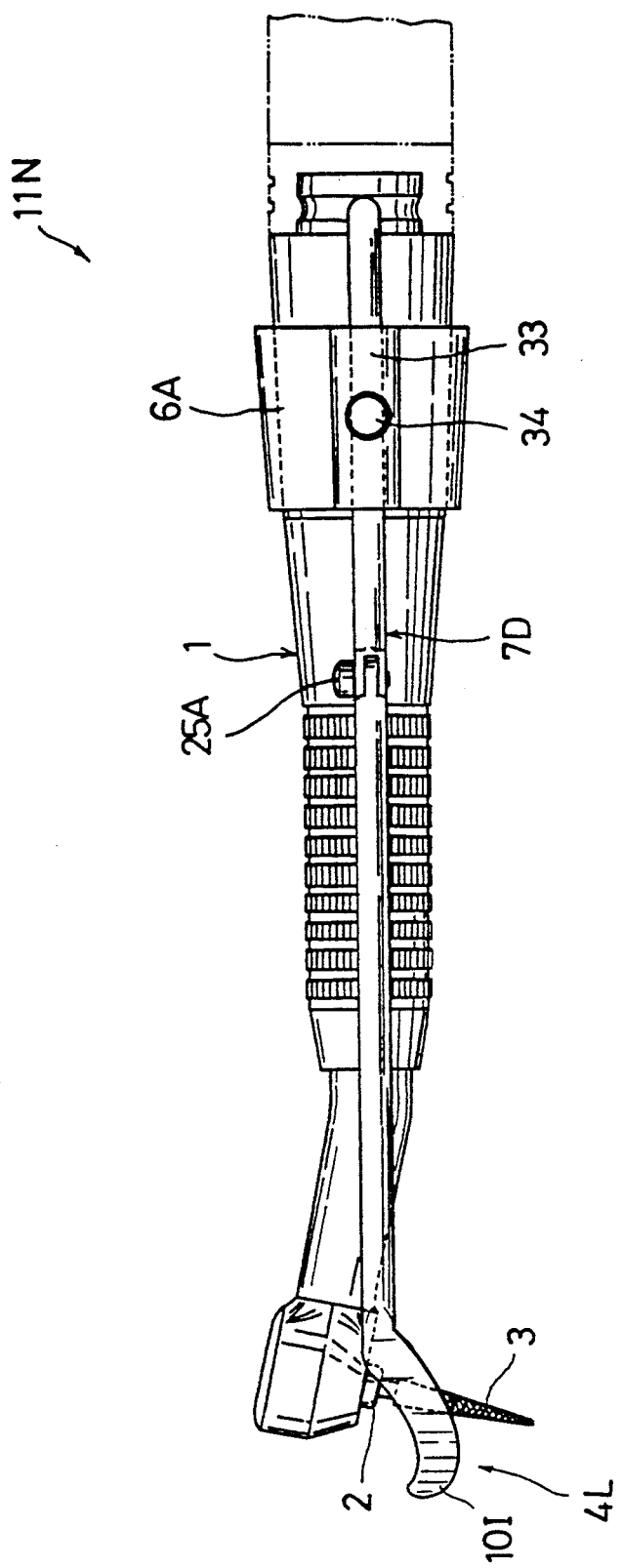
FIGS. 51 to 53 are explanatory views showing a fourteenth embodiment of the present invention.
Figure 52:
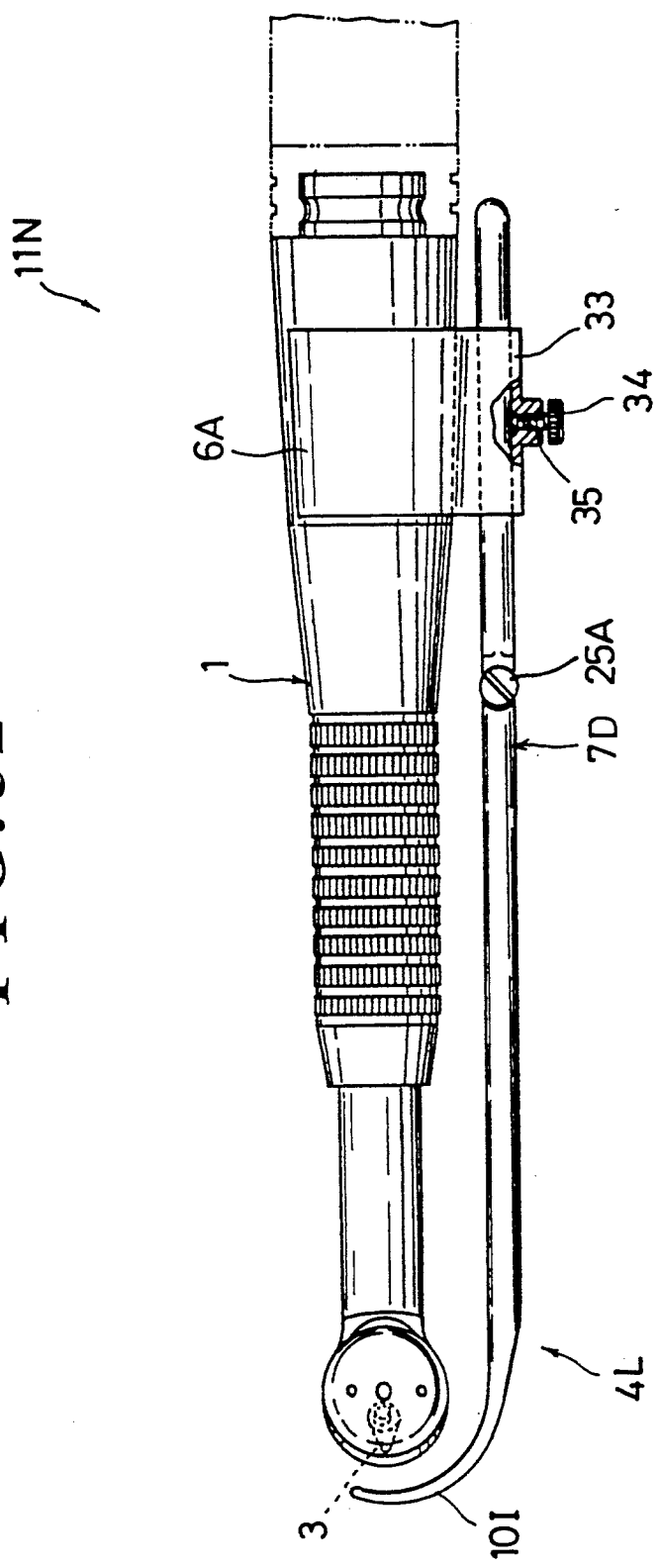
Figure 53:
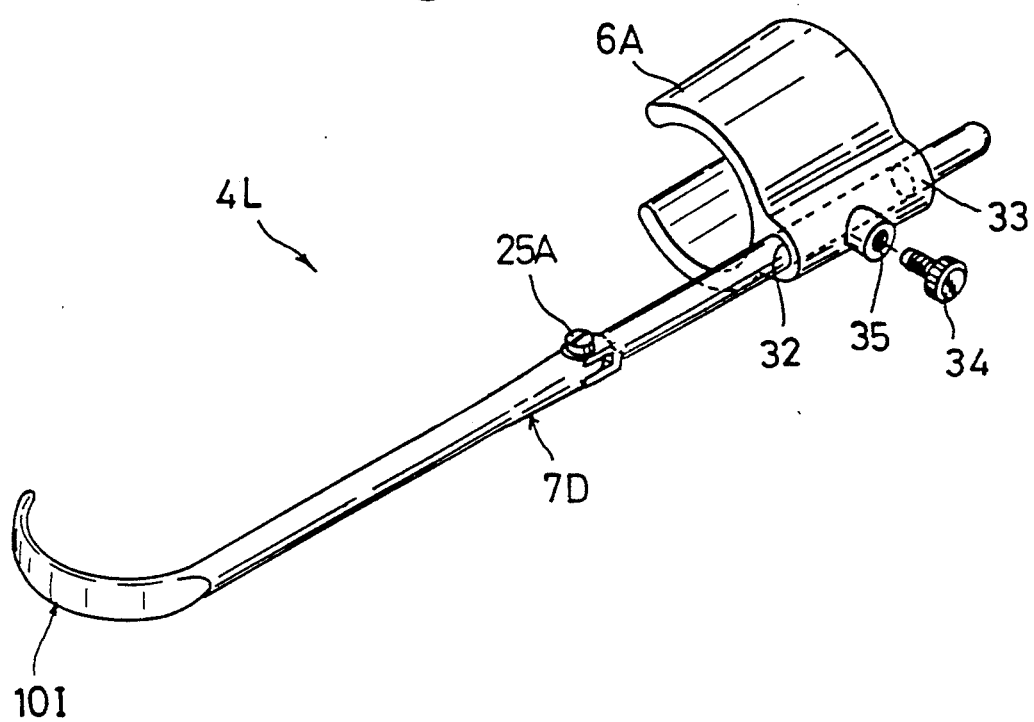
Figure 54:
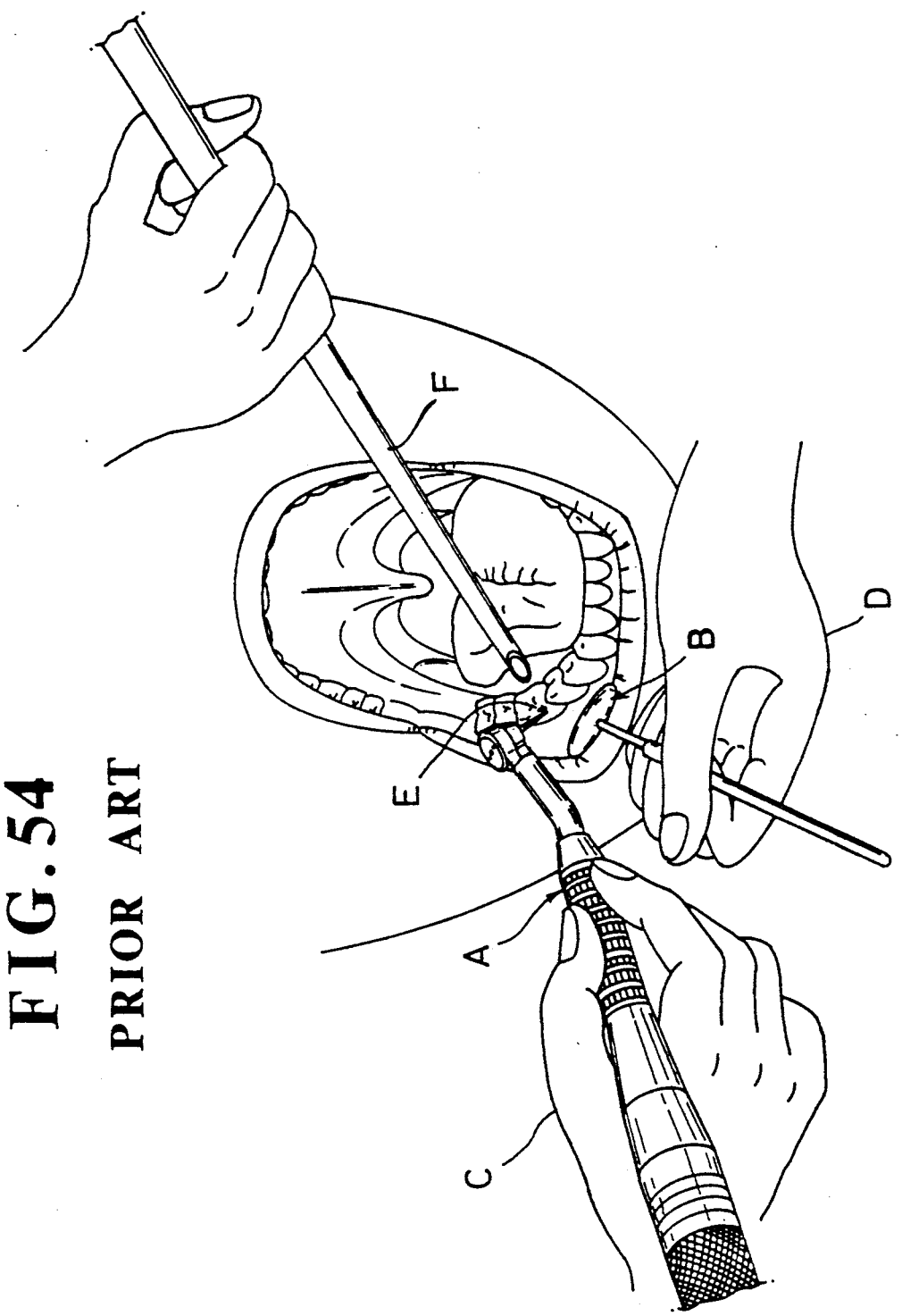
FIG. 54 is an explanatory view showing a traditional manner of cutting a decayed tooth.

A fourteenth embodiment of the present invention shown in FIGS. 51 to 53 differs from the ninth embodiment by the fact that the guard device 4H is replaced with a modified guard device 4L in which the foldable arm 7D has at its distal end an arcuate guard plate 10I extending to the front side of the cutting bit 3. Accordingly, a dental tool 11N provided with the guard device 4L can be protected from an innermost part of the mouth cavity wall.

It should be understood that the foregoing embodiments of the present invention are illustrative and not limitative of the shape of the fitting ring or member, the mounting of the fitting ring or member to the tool body, the coupling between the arm and the fitting ring or member, the construction of the arm, the coupling between the arm and the guard plate, and the shape of the guard described previously. Other changes and modifications will be possible without departing the scope of the present invention.

As set forth above, the present invention will ensure the following advantages.

(1) The dental power tool of the present invention comprises a tool body to be held by hand, a cutting bit detachably attached to a high-speed rotary head fixedly mounted to the front end of the tool body, and a guard device mounted to the tool body to be adjacent to the cutting bit and having a guard plate for keeping an obstacle, e.g. the tongue or a part of the inside wall of a lip, aside during treatment on a decayed tooth in the mouth. Hence, the dental power tool of the present invention allows a dentist to carry out a dental treatment without the help of a hygienist because its guard device presses away a possible obstacle which exists near the treated tooth.

The dental treatment will thus be conducted with efficiency.

(2) Due to the arrangement described in the paragraph (1), the dental treatment can be executed by a dentist alone with ease and precision regardless of troublesome cooperation with a hygienist.

(3) Due to the arrangement described in the paragraph (1), the guard device which is variable in position to and detachable from the tool body can arbitrarily be adjusted for ease of the dental treatment.

(4) Due to the arrangement described in the paragraph (1), the dental treatment can be conducted while giving no discomfort to a patient.

What is claimed is:

1. A dental power tool comprising a tool body; a high-speed rotary head attached to a front end of said tool body; a cutting bit detachably mounted to said rotary head; and a guard device detachably coupled to said tool body, said guard device having a fitting member to attach said guard device to said tool body, said fitting member being rotatably connected to said tool body thereby allowing said guard device to rotate 360° with respect to said tool body, an arm being slidable within said fitting member for extending and retracting said guard device, a screw being threaded in said fitting member operating to fix said arm in one of an extended and a retracted position, said arm having a first portion and a second portion pivotably connected to each other, thereby allowing said arm to swing distal and proximal with respect to said tool body, a guard plate being rotatably mounted to a front end of said arm, thereby allowing said guard plate to rotate 360° with respect to said arm, said guard plate having a semi-circular protuberance at its forward end and at each of its two lateral ends.

2. The tool of claim 1, wherein said guard plate has a reflective surface.

* * * * *